United States Patent
Havens et al.

(10) Patent No.: US 8,288,155 B2
(45) Date of Patent: Oct. 16, 2012

(54) BIOMOLECULAR ATTACHMENT SITES ON MICROELECTRONIC ARRAYS AND METHODS THEREOF

(75) Inventors: John R. Havens, San Diego, CA (US); Thomas J. Onofrey, San Marcos, CA (US); Charles H. Greef, Ramona, CA (US); Gregory J. Kevorkian, Temecula, CA (US); Jain Krotz, San Diego, CA (US); Kristie L. Lykstad, San Diego, CA (US); Daniel E. Raymond, San Diego, CA (US); Howard R. Reese, Poway, CA (US); Regina Rooney, La Jolla, CA (US); John J. Scott, Lafayette, IN (US)

(73) Assignee: Gamida for Life B.V., Rotterdam (NL)

( * ) Notice: Subject to any disclaimer, the term of this patent is extended or adjusted under 35 U.S.C. 154(b) by 977 days.

(21) Appl. No.: 11/777,919

(22) Filed: Jul. 13, 2007

(65) Prior Publication Data
US 2009/0069198 A1    Mar. 12, 2009

Related U.S. Application Data

(63) Continuation of application No. 09/410,368, filed on Sep. 30, 1999, now abandoned.

(51) Int. Cl.
*C12M 1/34* (2006.01)
*C12M 3/00* (2006.01)
(52) U.S. Cl. .................. 435/287.2; 435/283.1; 435/7.1; 436/518; 436/807
(58) Field of Classification Search ............... 435/287.2, 435/283.1, 7.1; 436/518, 807
See application file for complete search history.

(56) References Cited

U.S. PATENT DOCUMENTS

| 3,981,671 | A | 9/1976 | Edwards |
| RE30,130 | E | 10/1979 | Edwards |

(Continued)

FOREIGN PATENT DOCUMENTS

DE     19705303     1/1998

(Continued)

OTHER PUBLICATIONS

Anderson, et al., "Polymerized Lyotropic Liquid Crystals As Contact Lens Materials", Physica A, 1991, 176, 151-167, Elsevier Science Publishers B.V. (North Holland).

(Continued)

*Primary Examiner* — Melanie J Yu
(74) *Attorney, Agent, or Firm* — John P. White; Cooper & Dunham LLP

(57) ABSTRACT

Methods of addressing a biomolecule to a selectively addressable electrode are described. A permeation layer overlying a plurality of selectively addressable electrodes is provided. The permeation layer includes a reactive group that is adapted to bond to a biomolecule and that requires activation through a chemical transformation before bonding to the biomolecule. At least one selectively addressable electrode is biased such that a pH change occurs in an overlying solution of the at least one selectively addressable electrode. The reactive group in a portion of the permeation layer above the at least one selectively addressable electrode is then chemically transformed to an activated reactive group as a result of the pH change. A biomolecule is then bound to the permeation layer overlying the at least one selectively addressable electrode through the activated reactive group.

8 Claims, 29 Drawing Sheets

Electronic Array Activation

U.S. PATENT DOCUMENTS

| | | |
|---|---|---|
| 4,205,028 A | 5/1980 | Brueggemann et al. |
| 4,284,399 A | 8/1981 | Newcomb et al. |
| 4,472,124 A | 9/1984 | Kashihara et al. |
| 4,497,763 A | 2/1985 | Monnet |
| 4,552,633 A | 11/1985 | Kumakura et al. |
| 4,787,963 A | 11/1988 | MacConnell |
| 4,897,228 A | 1/1990 | Miwa et al. |
| 5,026,785 A | 6/1991 | Mage et al. |
| 5,034,428 A | 7/1991 | Hoffman et al. |
| 5,104,931 A | 4/1992 | Fleminger et al. |
| 5,147,297 A | 9/1992 | Myers et al. |
| 5,151,217 A | 9/1992 | Price |
| 5,164,162 A | 11/1992 | Ridenour |
| 5,171,782 A | 12/1992 | Candau et al. |
| 5,173,147 A | 12/1992 | Shimoyama et al. |
| 5,200,051 A | 4/1993 | Cozzette et al. |
| 5,212,050 A | 5/1993 | Mier et al. |
| 5,217,492 A | 6/1993 | Guire et al. |
| 5,223,441 A * | 6/1993 | Ullman et al. ............... 436/547 |
| 5,238,613 A | 8/1993 | Anderson |
| 5,244,799 A | 9/1993 | Anderson |
| 5,334,310 A | 8/1994 | Frechet et al. |
| 5,346,604 A | 9/1994 | Van Sin et al. |
| 5,405,618 A | 4/1995 | Buttery et al. |
| 5,445,934 A | 8/1995 | Fodor et al. |
| 5,453,185 A | 9/1995 | Frechet et al. |
| 5,460,872 A | 10/1995 | Wu et al. |
| 5,478,893 A | 12/1995 | Ghosh et al. |
| 5,491,097 A | 2/1996 | Ribi et al. |
| 5,496,509 A | 3/1996 | Yamamoto et al. |
| 5,510,074 A | 4/1996 | Rose |
| 5,521,229 A | 5/1996 | Lu et al. |
| 5,527,670 A | 6/1996 | Stanley et al. |
| 5,534,132 A | 7/1996 | Vreeke et al. |
| 5,543,098 A | 8/1996 | Myers et al. |
| 5,605,662 A * | 2/1997 | Heller et al. ............... 422/68.1 |
| 5,618,265 A | 4/1997 | Myers et al. |
| 5,624,973 A | 4/1997 | Lu et al. |
| 5,632,957 A | 5/1997 | Heller et al. |
| 5,648,482 A | 7/1997 | Meyer |
| 5,653,939 A | 8/1997 | Hollis et al. |
| 5,667,667 A | 9/1997 | Southern |
| 5,744,627 A | 4/1998 | Stowolitz et al. |
| 5,763,503 A | 6/1998 | Cowperthwaite et al. |
| 5,770,369 A | 6/1998 | Meade et al. |
| 5,777,148 A | 7/1998 | Stowolitz et al. |
| 5,783,054 A | 7/1998 | Raguse et al. |
| 5,798,276 A * | 8/1998 | Haugland et al. ............. 436/546 |
| 5,849,486 A | 12/1998 | Heller et al. |
| 5,889,104 A | 3/1999 | Rosenmayer |
| 5,919,523 A | 7/1999 | Sundberg et al. |
| 5,929,208 A | 7/1999 | Heller et al. |
| 5,952,398 A | 9/1999 | Dietz et al. |
| 5,981,734 A | 11/1999 | Mirzabekov et al. |
| 6,015,666 A | 1/2000 | Springer et al. |
| 6,017,696 A | 1/2000 | Heller |
| 6,031,277 A | 2/2000 | Sugiura et al. |
| 6,039,897 A | 3/2000 | Lochhead et al. |
| 6,048,690 A | 4/2000 | Heller et al. |
| 6,051,380 A | 4/2000 | Sosnowski et al. |
| 6,054,270 A | 4/2000 | Southern |
| 6,064,461 A | 5/2000 | Nishida |
| 6,066,448 A | 5/2000 | Wolfstadter et al. |
| 6,093,302 A | 7/2000 | Montgomery |
| 6,099,783 A | 8/2000 | Scranton et al. |
| 6,099,805 A | 8/2000 | Hartlove |
| 6,112,908 A | 9/2000 | Michaels |
| 6,121,027 A | 9/2000 | Clapper et al. |
| 6,121,489 A | 9/2000 | Dorner et al. |
| 6,136,444 A | 10/2000 | Kon et al. |
| 6,143,412 A | 11/2000 | Schueller et al. |
| 6,197,145 B1 | 3/2001 | Todd et al. |
| 6,197,881 B1 | 3/2001 | Cosnier et al. |
| 6,245,249 B1 | 6/2001 | Yamada et al. |
| 6,245,508 B1 | 6/2001 | Heller et al. |
| 6,264,825 B1 | 7/2001 | Blackburn et al. |
| 6,303,082 B1 | 10/2001 | John et al. |
| 6,306,348 B1 | 10/2001 | Havens et al. |
| 6,306,594 B1 | 10/2001 | Cozzette et al. |
| 6,444,111 B1 | 9/2002 | Montgomery |
| 6,458,547 B1 | 10/2002 | Bryan et al. |
| 6,458,584 B1 | 10/2002 | Mirzabekov et al. |
| 6,524,517 B1 | 2/2003 | John et al. |
| 6,615,855 B2 | 9/2003 | Lopez et al. |
| 6,673,433 B1 | 1/2004 | Saeki et al. |
| 6,673,533 B1 | 1/2004 | Wohlstadter et al. |
| 6,682,899 B2 | 1/2004 | Bryan et al. |
| 6,689,473 B2 | 2/2004 | Guire et al. |
| 6,733,643 B2 | 5/2004 | Matsumoto et al. |
| 6,761,816 B1 * | 7/2004 | Blackburn et al. ......... 205/777.5 |
| 6,767,816 B2 | 7/2004 | Kleveland et al. |
| 6,824,974 B2 | 11/2004 | Pisharody et al. |
| 6,838,053 B2 | 1/2005 | John et al. |
| 6,841,379 B2 | 1/2005 | Matson |
| 6,960,298 B2 | 11/2005 | Krotz et al. |
| 7,220,344 B2 | 5/2007 | Bentsen et al. |
| 7,270,850 B2 | 9/2007 | Krotz et al. |
| 2003/0190632 A1 * | 10/2003 | Sosnowski et al. ............... 435/6 |
| 2005/0266456 A1 | 12/2005 | Williams et al. |
| 2007/0034512 A1 | 2/2007 | Yamaoka et al. |

FOREIGN PATENT DOCUMENTS

| | | |
|---|---|---|
| EP | 0047645 B1 | 11/1984 |
| EP | 0226470 A2 | 6/1987 |
| EP | 0243501 A1 | 11/1987 |
| EP | 00446040 B1 | 11/1994 |
| JP | 55-152027 A | 11/1980 |
| JP | 56-167419 A | 12/1981 |
| JP | 59-215838 A | 12/1984 |
| JP | 59-227131 A | 12/1984 |
| JP | 01163049 A | 6/1989 |
| JP | 02292013 A | 12/1990 |
| WO | WO 93/22678 A2 | 11/1993 |
| WO | WO96/01836 | 1/1996 |
| WO | WO 96/07917 A1 | 3/1996 |
| WO | WO98/01221 | 1/1998 |

OTHER PUBLICATIONS

Antonietti, et al., "Polymerization in Microemulsions-A New Approach to Ultrafine, Highly Functionalized Polymer Dispersion", Macromol.Chem.Phys., 1995, 196, 441-446, Hüthig & Wepf Verlag, Zug.

Antonietti, et al., "Morphology Variation of Porous Polymer Gels by Polymerization in Lytropic Surfactant Phases, Macromolecules", 1999, 32, 1383-1389, American Chemical Society.

Antonietti, et al., "Polymer Gels With a Micron-sized, Layer-Like Architecture by Polymerization in Lyotropic Cocogem Phases", Langmuir, 1998, 14, 2670-2676, American Chemical Society.

Antonietti, et al., "Synthesis of Sponge-Like Polymer Dispersions Via Polymerization of Bicontinuous Microemulsions", Colloid Polym Sci, 1996, 274, 696-702, Steinkopff Verlag.

Antonietti, et al., "Microemulsions Polymerization: New Surfactant Systems by Counterion Variation", Adv. Mater., 1996, 8, 10, 840-844, VCH Verlagsgellshaft mbH, Weinheim.

Arenkov, et al., "Protein Microchips: Use for Immunoassay & Enzymatic Reactions", Analytical Biochemistry, 2000, 278, 123-131, Academic Press.

Bates, "Polymer-Polymer Phase Behavior", Science, Feb. 22, 1991, 25, 898-905.

Benedicto, et al., "Bicontinuous Cubic Morphologies in Block Copolymers & Amphiphile/Water Systems: Mathematical Description Through the Minimal Surfaces, Macromolecules", 1997, 30, 3395-3402, American Chemical Society.

Brinker, et al., *Sol-Gel Science*, 1990, Academic Press, San Diego.

Brown, "Dot & Slot Blotting of DNA, Current Protocols in Molecular Biology", 1993, Supplement 21, 2.9.15-2.10.16.

Burban, et al "Organic Microporous Materials Made by Bicontinuous Microemulsion Polymerization", AIChE Journal, Apr. 1995, 41, 4, 907-914.

Chieng, et al., "Microporous Polymeric Materials by Microemulsion Polymerization: Effect of Surfactant Concentrations", Langmuir, 1995, 11, 3321-3326.

Chieng, et al., "Morphology of Microporous Polymeric Materials by Polymerization of Methyl Methacrylate & 2-Hydroxyethyl Methacrylate in Microemulsions", Polymer, 1995, 36, 10, 1941-1946, Elsevier Science Ltd, Great Britain.

Chieng, et al., "Formation of Microporous Polymeric Materials by Microemulsion Polymerization of Methyl Methacrylate & 2-Hydroxyethyl Methacrylate", Journal of Applied Polymer Science, 1996, 60, 1561-1568, John Wiley & Sons, Inc.

Hentze, et al, "Synthesis of Organic Polymer Gels in Microemulsions & Lyotropic Mesophases", Ber.Bunsenges. Phys. Chem., 1997, 101, 11, 1699-1702, Wiley-VCH, Weinheim.

Kempe, et al, "Receptor Binding Mimetics: A Novel Molecularly Imprinted Polymer", Tetrahedron Letters, 1995, 36, 20, 3563-3566.

Lee, et al., "Polymerization of Nonlamellar Lipid Assemblies", J. Am. Chem. Soc., 1995, 117, 5573-5578.

Lindblom, et al, "Cubic Phases & Isotropic Structures Formed by Membrane Lipids-Possible Biological Relevance", Biochimica et Biophysica Acta, 1989; 988, 221-256, Elsevier Science Publishers B.V. (Biomedical Div).

Liu, et al. "Effect of Non-Ionic Surfactants on the Formation of DNA/Emulsion Complexes and Emulsion-Mediated Gene Transfer", Pharmaceutical Research, vol. 13, No. 11, 1996, pp. 1642-1646.

O'Connell, et al, "Polyacrylamide Gels With Modified Cross-Linkages", Analytical Biochemistry, 1976, 76, 63-73, Academic Press, Inc.

Odian, *Principles of Polymerization*, $3^{rd}$ Edition, (John Wiley & Sons: New York, New York), 1991, 232.

Ogawa, et al., "Preparation of Self-Standing Transparent Films of Silica-Surfactant Mesostructured Materials and the Conversion to Porous Films", Adv. Mater., vol. 10, No. 14, 1998, pp. 1077-1080.

Paul, et al., "Cubic Phase Polymer Hydrogels: Templated Polymerization from Surfactant Mesophases", AIChE Meeting, Dallas, Texas, Oct. 31-Nov. 5, 1999, 71.

Peters, et al., "Rigid Macroporous Polymer Monoliths", Adv. Mater, 1999, 11, 14, 1169-1181, Wiley-VCH, Weinheim.

Raj, et al., "Formation of Porous Polymeric Structures by the Polymerization of Single-Phase Microemulsions Formulated with Methyl Methacrylate & Acrylic Acid", Langmuir, 1991, 7, 2586-2591, American Chemical Society.

Raj, et al.,"Polymerization of Microstructured Aqueous Systems Formed Using Methyl Methacrylate & Potassium Undeconoate", Langmuir, 1992, 8, 1931-1936.

Raj, et al., "Synthesis of Porous Polymeric Membranes by Polymerization of Micro-emulsions", Polymer, 1993, 34, 15, 3305-3312, Butterworth-Heinemann Ltd.

Raj, et al., "Microcellular Polymeric Materials From Microemulsions: Control of Microstructure & Morphology", Journal of Applied Polymer Science, 1993, 47, 499-511, John Wiley & Sons, Inc.

Righetti, et al., "On the Limiting Pore Size of Hydrophilic Gels for Electrophoresis & Isoelectric Focusing", Journal of Biochemical & Biophysical Methods, 1981, 4, 347-363.

Righetti, et al., "Towards New Formulations for Polyacrylamide Matrices, As Investigated by Capillary Zone Electrophoresis", Journal of Chromatography, 1993, 638, 165-178, Elsevier Science Publishers B.V.

Rill, et al., "Templated Pores in Hydrogels for Improved Size Selectivity in Gel Permeation Chromatography", Analytical Chemistry, Jul. 1, 1998, 70, 13, 2433-2438.

Samal, et al., "Electroinitiated Polymerization of Acrylamide in Acetonitrile Medium", J. Polym. Sci. Polym., 26, 1988, 1035-1049.

Sasthav, et al., "Characterization of Microporoith Polymeric Materials: Pore Continuity & Size Distribution Via Thermal Analysis", Journal of Colloid & Interface Science, Sep. 1992, 152, 2, 376-385.

Seddon, "Structure of the Inverted Hexagonal ($H_{II}$) Phase, & Non-Lamellar Phase Transitions of Lipids", Biochimica et Biophysica Acta, 1990, 1031, 1-69, Elsevier Science Publishers BV (Biomedical Div).

Shiyakhtenko, et al., "Atomic Force Microscopy Imaging of DNA Covalently Immobilized on a Functionalized Mica Substrate", Biophysical Journal, Jul. 1999, 77, 568-576, Biophysical Society.

Sigma-Aldrich Brij, 700 Specification Sheet, http://www/sigmaaldrich.com/catalog/search/SpecificationSheetPage/Aldrich/466387, 2007, 1 page.

Sosnowski et al., "Rapid Determination of Single Base Mismatch Mutations in DNA Hybrids by Direct Electric Field Control", Proc. Natl. Acad. Sci. USA, Feb. 1997, 94, 1119-1123.

Srisiri, et al., "Polymerization of the Inverted Hexagonal Phase", J. Am. Chem. Soc., 1997, 119, 4866-4873, American Chemical Society.

Svec, et al., "Molded Rigid Monolithic Porous Polymers: An Inexpensive, Efficient & Versatile Alternative to Beads for the Design of Materials for Numerous Applications", Ind. Eng. Chem. Res., 1999, 38, 34-48, American Chemical Society.

Vasiliskov, et al., "Fabrication of Microarray of Gel-Immobilized Compounds on a Chip by Copolymerization", BioTechniques, Sep. 1999, 27, 3, 592-605.

Viklund, et al., "Monolithic, 'Molded', Porous Materials With High Flow Characteristics for Separations, Catalysis, or Solid-Phase Chemistry: Control of Porous Properties During Polymerization", Chem. Mater., 1996, 8, 744-750, American Chemical Society.

ProZyme Streptavidin Specification Sheet http/www. Prozyme.com/pdf/sa10.pdf, Mar. 31, 2007.

Wang et al. (2005), "Carboxyfluorescein Diacetate Succinimidyl Ester Fluorescent Dye for Cell Labeling" Acta Biochimica et Biophysica Sinica, 37(6): 379-385.

Chen et al. (2001), "Noncovalent Sidewall Functionalization of Single-Walled Carbon Nanotubes for Protein Immobilization" J. Am. Chem. Soc., 2001, 123: 3838-39.

* cited by examiner

General Schemes

Scheme 1

Scheme 2

Scheme 3

| | | |
|---|---|---|
| Specific | column 1 | 7962 |
| | column 3 | 30936 |
| Nonspecific | column 2 | 7013 |
| | column 4 | 7500 |
| acetal | column 5 | 1494 |

S/NS ratio for columns 3/4 = 4.1
All numbers are in MFI/s

BIOMOLECULAR ATTACHMENT SITES ON MICROELECTRONIC ARRAYS AND METHODS THEREOF

This is a continuation of U.S. application Ser. No. 09/410,368, filed Sep. 30, 1999, now abandoned which is hereby expressly incorporated by reference in its entirety.

FIELD OF THE INVENTION

This invention relates to the incorporation of functional groups in association with the permeation layer of an electronically addressable microarray. More specifically, this invention relates to microelectronic array permeation layers and their fabrication wherein there is included specific functional groups that may be activated at specified locations on the microarray and/or polymerized to high density for attaching biomolecules.

BACKGROUND OF THE INVENTION

The following description provides a summary of information relevant to the present invention. It is not an admission that any of the information provided herein is prior art to the presently claimed invention, nor that any of the publications specifically or implicitly referenced are prior art to the invention.

The art of attachment chemistry for macroscopic and microscopic arrays has received much attention in recent years. However, as requirements for assay sensitivities have increased, the need for attachment chemistries that are able to provide greater specificity in attachment of biomolecules, as well as greater density of attached biomolecules, has also increased.

Although covalent and non-covalent attachment chemistries have become well developed, few advances have overcome some of the fundamental difficulties experienced with electronic microarrays. For example, problems with present electronic microarrays include non-specific binding of biomolecules outside specific capture/detection sites and the inability to control passive binding of such biomolecules before, during, and after electronic addressing. These problems result in less than ideal discrimination of target molecules from nontarget molecules. Likewise, attachment chemistries currently in use have made it difficult to manipulate unused capture sites during multiple site or sequential site addressing of target molecules without encountering undesired passive binding of nontarget molecules to the capture sites.

In providing a solution to the problems of low specificity of binding and discernment of target from nontarget, we provide attachment chemistry for attaching biomolecules that provides specificity of binding as well as enhanced target discernment at the capture sites by a method which significantly increases the density of target binding sites on the microarray. Moreover, this method provides for localizing the deposition of target binding sites using the electrodes of the microarray.

While much of the art involving microarray deposition concerns masking techniques to enhance specificity of binding, one method has been used to electrochemically treat the surface desired to be patterned with chemical moieties. In PCT application WO93/22480 by Southern is disclosed a method of electrochemically patterning a surface wherein an electrode grid is positioned adjacent to the surface desired to be patterned in solution and in direct contact with the electrolyte. The electrode grid provides an electronic potential that directs deposition of molecules, removal of molecules, or chemical modification of molecules, on the substrate surface. Following such electronic treatment process, the grid is removed. Although such a method provides a means for patterning a nonelectronic surface, it is applicable only to passive array formats. Additionally, the method can only be applied in initial manufacture of an array and not applied to an array in an active "on-demand" manner.

Other art has centered on deposition chemistry. For example, Sundberg et al. in U.S. Pat. No. 5,919,523 discloses attachment chemistry typically used for attaching molecules directly to derivatized glass slides. Such chemistry is designed for attaching and synthesizing nucleic acid sequences wherein one useful aspect is a need for wettability of the substrate surface. Such chemistry is further distinguished from that used in the present invention in that the electronic microarrays of the present invention require a porous permeation layer above the electrodes which comprises reactive moieties that participate in the attachment and polymerization chemistry scheme of the invention.

In both of the above examples, as in the case with typical attachment chemistries, the levels of binding of attached molecules is limited to the number of reactive moieties present on the substrate surface. Thus, there remains a need in general for a method of derivatizing a substrate surface in such a way that attachment sites for binding molecules of interest to the substrate is dramatically increased. We have found such a method with respect specifically to substrates comprising permeation layers of electronically addressable microarrays.

As is well understood in the art of hybridization and detection of target molecules using nucleic acid probes, it is important to have a high density of capture probe binding on the detection surface of the microarray. In conventional surface modification techniques, the available groups on the surface are derivatized to include functional moieties that can bind to capture probes. The capture probe binding in turn depends on the number and availability of derivatized groups or binding sites on the detection surface. In many applications, such as infectious disease detection, genomic research, etc., the ability to detect very low levels of nucleic acid is necessary. To this end, the current invention provides a novel method of surface modification wherein polymers of functional groups having multiples of attachment moieties for binding capture probes (i.e. derivatized biomolecules) are on the surface of the permeation layer. The availability of such attachment moieties may also be placed at predetermined positions on the array. This provides for increased discrimination between specific and nonspecific binding of biomolecules on the microarray.

SUMMARY OF THE INVENTION

Definitions

"Derivatized biomolecules" as used herein means molecules that are used to contact and detect the presence of molecular entities in a test sample. Generally, these include, at least in part, molecules such as nucleic acids, proteins, peptides, enzymes, and antibodies attached to chemical moieties such as streptavidin, biotin, phenyl boronic acid (PBA), and salicylhydroxamic acid (SHA). Derivatized biomolecules also include oligonucleotides containing oxidized ribose, amine terminations, or any entity of the well known bioconjugate pairs as outlined by Hermanson (Hermanson, G. T. *Bioconjugate Techniques* copyright 1996, Academic Press, San Diego, Calif.) herein incorporated by reference, and/or alternative nucleic acid structures such as pRNAs (in reference to pRNAs as described in co-pending application Ser. No. 09/374,338 filed Aug. 13, 1999 herein incorporated by reference). Generally, attachment of the chemical moieties to the biomolecules comprises a covalent bond. With respect to attachment of derivatized biomolecules to the microarray, such attachment may use either an 'A' or an R moiety and may use either a covalent or a noncovalent bond.

"Microarray" as used herein means an electronically addressable microarray such as an array designated the "APEX chip" as in U.S. Pat. No. 5,632,957 herein incorporated by reference.

"Permeation layer" as used herein means a porous matrix coating overlying a spaced electrode array on an electronically addressable microchip such as the above defined microarray. The permeation layer may comprise any number of materials. In a preferred embodiment, the layer comprises a base polymer layer comprising materials such as agarose or polymerized acrylamide or methacrylamide hydrogels having biomolecule attachment moieties in the form of R moieties either copolymerized within the base permeation layer matrix or present as a top or surface layer. Such moieties may comprise thiols, ketones, aldehydes, maleimide, amines, hydrazide, hydrazine, methacrylamide-SHA, halo-acetamide, bromopropylamine, and bromoacetyl-propyl-methacrylamide as well as those outlined by Hermanson (ibid, Hermanson). The permeation layer further contemplates inclusion of functional groups either copolymerized with or grafted onto the permeation layer polymer matrix. Where grafted, the functional groups may be grafted in a polymerization reaction such that the groups are polymerized in the same reaction as the grafting reaction, or may be grafted in a previously polymerized form. Still further, in its most complete form, the permeation layer contemplates attachment of biomolecules.

"Mean fluorescence intensity" or MFI as used herein means the average of the pixel count values during fluorescence detection over a region of interest upon normalizing the detection camera integration time to one second. The value ranges will vary according to the makeup of the permeation layer. MFI values from one experiment to another can fluctuate by as much as a factor of 10,000 due to many factors including light settings, filters, integration time before normalization, light intensity and initial fluorophore concentration. A direct comparison of MFI values from one experiment to another is not recommended, while comparison of differentiating signals within a given set of experiments is allowed.

"Functional group" means any chemical moiety capable of undergoing a chemical transformation.

Embodiments of the current invention provide permeation layers and methods for permeation layer fabrication for use on electronically addressable microarrays wherein functional groups, designated 'P—X—R', are incorporated into the permeation layer by copolymerization during fabrication of the layer, or by grafting onto a preformed base permeation layer. These functional groups are versatile but simple in design. They contain two reactive centers (i.e., the P moiety and the R moiety) that generally perform separate functions but in some circumstances may perform similar functions.

The R moieties may bind to either derivatized biomolecules or to additional functional groups of an identical P—X—R formula or to functional groups of the same formula but having a variation in the P and/or R moiety. Where the R moieties bind to additional P—X—R groups, a grafting method is provided comprising a polymerization reaction in either a solution or a slurry process described below, wherein the R moiety reacts with a P or the R moiety of the added group. In a further embodiment, the P moiety may react with P or the R moieties of a second added group and so forth. The functional groups to be added may also already be polymerized prior to addition to the base permeation layer. Whether the R moiety is to bind to a derivatized biomolecule or to additional functional groups, the R moiety may bind directly, due to the chemical structure of the R moiety (i.e., the R group does not need to be "activated"), or may be of such chemical makeup that it will bind only after being activated. Activation may be induced either nonspecifically or specifically. Where activation is initiated nonspecifically, the R groups are activated by generating a pH change throughout a solution overlying the microarray. Where activation is initiated specifically, the R groups are activated by generating a pH change in a solution overlying the microarray only at positions directly above specific locations on the microarray corresponding to the positions of the electrodes underlying the permeation layer.

The P moieties are designed to participate in polymerization reactions as a single monomer or with other P moieties of an additional P—X—R. They may also bind either to reactive centers on the base permeation layer (i.e., 'A' moieties), or to R moieties of functional groups previously incorporated onto the permeation layer. In this case, the P moiety of the functional group being attached to the permeation layer ('A' or R) may either already be incorporated into a polymer but available for attaching to an R or an 'A', or the P moiety may attach while simultaneously participating in a polymerization reaction.

As is the case with binding to R groups discussed above, the polymerization reaction may be carried out in either a solution or a slurry process, wherein the P moiety may react with an 'A', or an R moiety, and/or a P moiety of an added functional group. In the case where P becomes attached to an 'A' or an R moiety, such reactive centers 'A' or R moieties may comprise either a chemical moiety that does not need to be activated or alternatively one that requires activation. In the case where P is involved in a polymerization with another P moiety, the solution or slurry grafting may be initiated nonspecifically by using a 'polymerization initiator reactive molecule' that is sensitive to heat and/or radiation which can be applied across the entire microarray.

Initiation of polymerization, as well as activation of 'A' and R moieties, may be initiated specifically or nonspecifically as in the case of the R moieties noted above. However, with respect to specific initiation, polymerization may be carried out in several ways. For example, in one embodiment chemical initiators that are sensitive to electronically generated pH changes in the solution overlying the microarray, rather than heat or radiation, may be used. In another embodiment ultraviolet radiation may be used to initiate polymerization wherein the use of 'directed' radiation is required in order that polymerization occur only above the electrodes. In still another embodiment, polymerization may be specifically directed to predetermined locations by grafting the polymerizing P moiety to specifically activated 'A' or R moieties.

The X moiety serves as a linker moiety that normally is not reactive with other chemical moieties or functional groups. In one embodiment, the X moiety serves as a linker, while in another embodiment the X moiety servers as a spacer element, while in still another embodiment, X may be a chemical bond.

As will be understood by one of skill in the art, each of 'A', P, X and R as described below provides for addition of high densities of R moieties that are available for binding derivatized biomolecules, thereby increasing the specificity and sensitivity of the electronically addressable microarray.

As is understandable to one skilled in permeation layer art, permeation layers of electronically addressable microchips may comprise any number of molecular structures. In preferred embodiments, such layers generally comprise a base permeation layer comprising a porous material. Such materials suitable for use in the present invention includes such materials as agarose, chitosan, polymers formed from acrylamide, methacrylamide, polyethylene glycols, vinyl pyrrolidone, and sol-gels. Base permeation layers made of such materials provide several benefits to electronic microarrays. For example, they provide insulation between the electrode and the overlying solution. They also provide a porous matrix suitable for allowing ion exchange between the electrode surface and the overlying solution. They also provide a backbone having reactive centers 'A' that may be used for binding chemical moieties (e.g. a functional group) for attaching various molecules of interest such as proteins and nucleic acids; inorganic materials, such as sol-gels, may also be used to form the base permeation layers as described in copending application Ser. No. 09/354,931 filed Jul. 15, 1999 herein incorporated by reference. These porous glasses may be reacted with silane coupling agents to introduce 'A' and R moieties.

With respect to the current invention, in one embodiment, reactive centers, designated 'A' moieties, of the base permeation layer matrix are provided for attaching molecules of interest, such as functional molecules having the formula P—X—R. The 'A' moieties may be designed so that they will react with and attach to the functional molecules directly, or may be designed so that they must be activated prior to participation in further deposition chemistry. In one preferred embodiment, the 'A' moieties may be nonspecifically activated so that any activated 'A' moiety on the array may participate in deposition chemistry. In another preferred embodiment, the 'A' moieties may be specifically activated at predetermined sites (i.e., capture sites) by providing an electronic potential to the underlying microelectrodes located under the permeation layer matrix so that deposition chemistry will only occur at those specifically activated sites. In both specific and nonspecific activation of the 'A' moieties, it is contemplated that a solution overlying the permeation layer is made to experience a change in pH conditions (across the entire array in the case of nonspecific and only at capture sites in the case of specific activation) favorable to activation of the 'A' moieties. In the case of nonspecific activation, the pH change is brought about by exchanging solution content while in the case of specific activation, the pH change is brought about by the electronic potential provided at the capture sites.

In another embodiment, the 'A' moieties may be reacted with functional groups having the formula P—X—R during formation of the base permeation layer wherein after formation the permeation layer has derivatized thereon instead of 'A' moieties available for further deposition chemistry, P—X—R moieties. In this embodiment, the P moiety is attached to the permeation layer base and the R moiety is available for further deposition chemistry. In one aspect of this embodiment, the R moiety may be designed for reaction directly with either a derivatized biomolecule or additional functional groups. In another aspect of this embodiment, the R moiety may be designed to require that it be activated prior to participating in further deposition chemistry of the biomolecules and functional groups. In one instance, as described below, the derivative moiety attached to the biomolecule may be considered a P—X—R functional group. As with the 'A' moieties, in the case where activation is necessary, activation may be initiated either specifically or nonspecifically.

In another embodiment, deposition chemistry involves the solution or slurry grafting of functional groups having the formula P—X—R, in either a previously polymerized state or in a polymerization reaction, to either 'A' or R moieties located on the permeation layer. Whether the added groups are previously polymerized or are polymerized during the grafting procedure, the grafting occurs between a P moiety of a functional group being added and either an 'A' or R group. As stated above, the binding between 'A' or R and P may require activation of the 'A' or R depending upon their respective chemical makeup. Where activation is required, such activation may be initiated either specifically or nonspecifically. Nonspecific activation may be carried out by a pH change, either high or low, in a solution overlying the microarray. Specific activation may be initiated by biasing the electrodes of specific capture sites to induce a pH change at those sites.

Coincidental to activation of 'A' or R, if necessary, or where no activation is necessary, grafting of the functional groups to the 'A' and/or R moieties may be initiated using either of the slurry or the solution methods of the invention. Since the 'A' or R groups may require activation, the grafting may be carried out in either a specific or a nonspecific manner. Additionally, the grafting may comprise grafting of a previously polymerized P—X—R matrix, or grafting at the same time the functional group is being polymerized. Where polymerization is to occur during grafting, a chemical polymerization initiator that is activated by heat or radiation is preferred. This allows the versatility in the grafting process to be carried out in a specific manner. In other words, use of an 'A' or R that requires activation may be specifically activated to react with polymerizable functional groups in a slurry or solution graft reaction to graft functional groups at specific locations on the array.

In the slurry grafting method, the functional groups are layered over the array in a concentrated form with an initiator molecule. Under appropriate reaction conditions, the initiator and P moieties of the functional molecules react to form a polymer of the functional molecule bonded to the permeation base layer. In the solution grafting method, the initiator molecule and the functional molecule are layered over the array in a soluble mixture. In either case, high density grafting of functional groups occurs providing high density biomolecule attachment sites. The grafting may be carried out either specifically, using electronic biasing for polymerization concentrated at capture sites, or nonspecifically across the entire array.

In another embodiment, the invention contemplates the attachment of derivatized biomolecules to the microarray. As stated previously, the attachment of such a molecule is through an R moiety. In either case, attachment may comprise either a covalent or a noncovalent bond depending upon the chemistry used. Since the functional group is generally contemplated to be added in multiples, the capacity for attaching biomolecules to the array is dramatically increased to a very high density.

In yet another embodiment, the 'A' or R of the permeation layer comprise thioester moieties that are pH labile (high or low pH). In this embodiment, the specific electronically addressable capture sites may be positively or negatively biased to activate the thioesters at predetermined capture sites to allow binding of either P—X—R functional groups or derivatized biomolecules.

With respect to the 'A' moiety on the permeation layer backbone, generally, 'A' comprises a reactive center that can be used to bind additional functional groups. This may comprise either a carbon atom in the polymer backbone that is sensitive to react in a free radical reaction, or a chemical moiety attached to the polymer backbone, such as tertiary carbons that will react either directly, or following sensitization (i.e., activation), become activated wherein activation generally comprises the formation of a species that will participate in a further reaction with a P moiety. Included in the definition of 'A' are the well known bioconjugate pairs (ibid, Hermanson) which are used to couple biomolecules together as would be recognized by one skilled in the art.

In yet another embodiment, the 'A' or R of the permeation layer comprise acetal moieties that may be hydrolyzed using an acidic solution or electronic biasing to yield aldehyde functionality for attachment of derivatized biomolecules or P—X—R functional groups at specified capture sites. In a preferred embodiment of this aspect, the capture sites are electronically biased such that water in solution is oxidized to generate a low pH for the acidic hydrolysis of acetal groups to give aldehyde groups that may be used to react with the derivatized biomolecules or functional groups.

In still another preferred embodiment, grafted polymerized functional groups overcome prior problems associated with the permeation layer swelling. In still another embodiment, the use of polymerized functional groups, whether bonded using electronic or nonelectronic activation of reactive moieties allows for decreased background fluorescence as compared with nonpolymerization techniques. The methods of the invention further contemplate use of other grafting methods including plasma grafting, wherein a gas is exposed to an electrical discharge at low pressure. The ionized gas then initiated grafting and subsequent polymerization of a monomer onto an existing polymer. (for further details see Odian, G. *Principles of Polymerization* $3^{rd}$ ed. Copyright 1991, by John Wiley and Sons, New York, N.Y.; p. 232 and references therein herein incorporated by reference).

In yet another embodiment, the methods of the invention provide for attachment of high biomolecule densities on the array.

BRIEF DESCRIPTION OF THE DRAWINGS

FIG. 1A is a photomicrograph wherein columns 2 and 4 are duplicates for specific binding while columns 3 and 5 are duplicates for nonspecific binding. Column 1 is a zero binding control in which no labeled probe was addressed.

FIG. 3A is a photomicrograph wherein columns 1 and 3 are duplicates of specific binding while columns 2 and 4 are duplicates of nonspecific binding.

FIG. 13 specifically shows passive attachment onto pads which were electronically deprotected. FIG. 14 displays the required electronic conditions for sufficient deprotection of the acetal to an aldehyde. FIGS. 15 and 16 show specific and nonspecific attachment of labeled capture molecules onto a deprotected acetal moiety.

FIG. 17A is a photomicrograph wherein column 3 is specific binding, while columns 1 and 5 are duplicates of nonspecific binding.

FIG. 20 shows more detail of chemical structure than FIG. 19.

FIG. 24A is a photomicrograph wherein columns 1 and 3 are specific binding, while columns 2 and 4 are nonspecific binding. Column 5 was not addressed.

DETAILED DESCRIPTION OF THE PREFERRED EMBODIMENTS

Figure 1A:
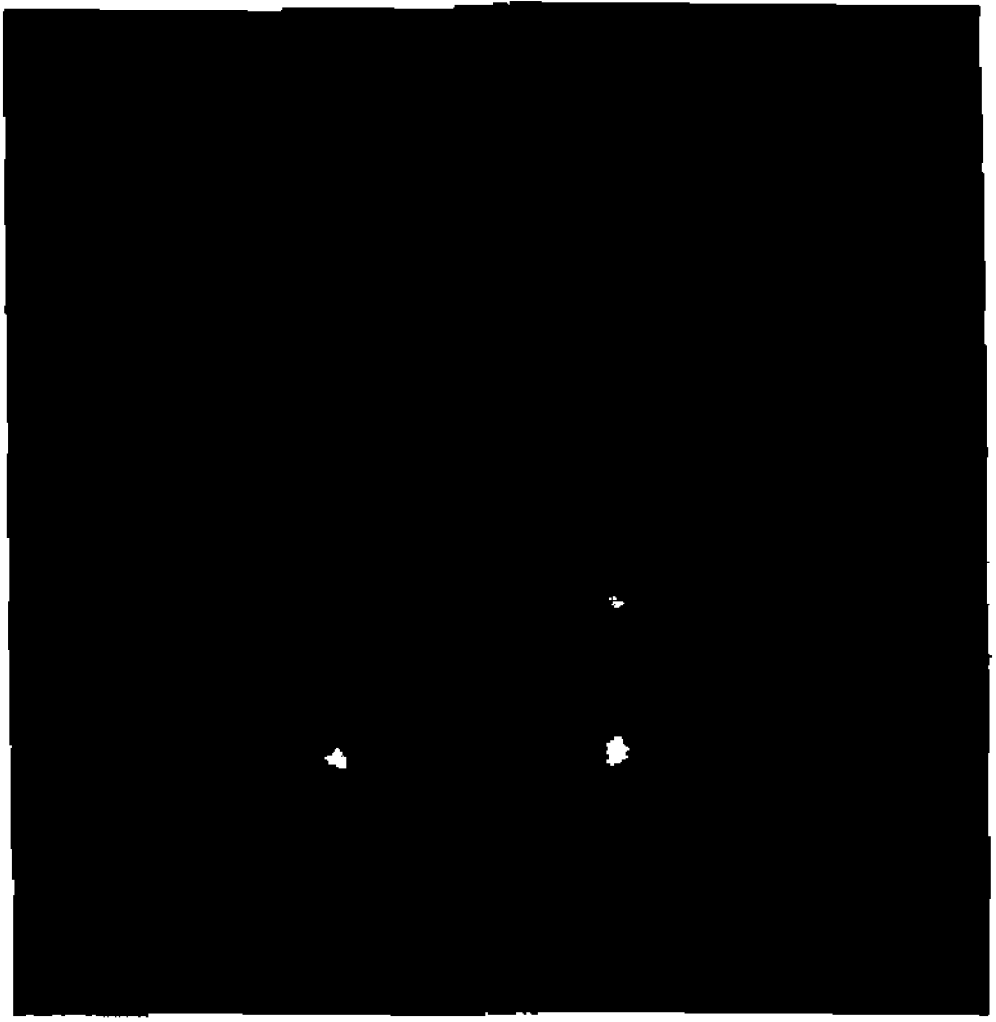
FIGS. 1A and B show results of probe attachment density following attachment of maleimide on the array surface.

According to the embodiments of the current invention, permeation layer coated electronic microarrays and methods of making such microarrays are provided wherein the permeation layers comprise functional groups for attaching high densities of derivatized biomolecules. With respect to the making of such arrays, functional groups comprise chemical moieties having a simple but versatile formula that allows the groups to be incorporated on the permeation layer in several ways.

The functional groups have the formula:

wherein,

P comprises a chemical moiety the design of which may vary depending upon the nature of the moiety with which it is desired to react. Regardless of the moiety with which P is desired to react, the P moiety always includes a reactive center that may participate in bonding to another P reactive center in a polymerization reaction, and/or bond to a reactive center designated 'A' of the permeation layer matrix, and/or bond to an R moiety of another functional group. Where the P moiety is intended to bond to another P moiety reactive center or intended to bond to a reactive center 'A', P is selected from the group consisting of alkenyl moieties including but not limited to substituted or unsubstituted α,β,unsaturated carbonyls wherein the double bond is directly attached to a carbon which is double bonded to an oxygen and single bonded to another oxygen, nitrogen, sulfur, halogen, or carbon; vinyl, wherein the double bond is singly bonded to an oxygen, nitrogen, halogen, phosphorus or sulfur; allyl, wherein the double bond is singly bonded to a carbon which is bonded to an oxygen, nitrogen, halogen, phosphorus or sulfur; homoallyl, wherein the double bond is singly bonded to a carbon which is singly bonded to another carbon which is then singly bonded to an oxygen, nitrogen, halogen, phosphorus or sulfur; alkynyl moieties wherein a triple bond exists between two carbon atoms. Where the P moiety is intended to bond to an R moiety, P is selected from the group consisting of a substituted or unsubstituted α,β,unsaturated carbonyls, vinyl, allyl and homoallyl groups and alkynes. Within this embodiment, P can also be selected from the group consisting of acetal, epoxide, ester, carboxylic acid, amide, halo-acetamide, thiol, phosphorothiolate monoester, thioester, disulfide, aldehyde, ketone, hydrazide, hydrazine, and amines; as well as those listed in Hermanson (ibid, Hermanson). Depending upon which of the P moieties are chosen and the reaction conditions used, the reactive center of P may become reactive to participate in a polymerization and/or coupling reaction. As discussed in the examples below, polymerization conditions can include use of a slurry grafting method or a solution grafting method. In a preferred embodiment, the P moiety is designed to participate in a polymerization reaction and become bonded to either an 'A' or an R moiety that has already been incorporated into the permeation matrix either due to the nature of the matrix backbone itself (in the case of 'A') or due to functional groups being either copolymerized into the layer during fabrication or prior grafting (in the case of an R).

X is a moiety selected from the group consisting of a chemical bond, an alkyl of 1-10 carbon atoms, an alkenyl of 2-10 carbon atoms, alkyl esters, ketones, amides, thioesters, alkyl ethers, amido groups, carbonyls, and/or any combinations thereof.

As used herein, alkyl denotes straight-chain and branched hydrocarbon moieties such as methyl, ethyl, propyl, isopropyl, tert-butyl, isobutyl, sec-butyl, neopentyl, tert-pentyl and the like. Such alkyls may be substituted with a variety of substituents including but not limited to hydroxy, oxo, amino, thio, cyano, nitro, sulfo and the like. Alkenyl denotes a hydrocarbon wherein one or more of the carbon-carbon bonds are double bonds and the non-double bonded carbons are alkyl or substituted alkyl. Alkenyl hydrocarbons groups may be straight-chain or contain one or more branches. Amino refers to moieties including a nitrogen atom bonded to 2 hydrogen atoms, alkyl moieties and combination thereof. Amido refers to moieties including a carbon atom double bonded to an oxygen atom and single bonded to an amino moiety.

R is a chemical moiety for attaching, either covalently or non-covalently, a biomolecule or for bonding to P—X—R groups. Where R is intended to be bonded to P—X—R functional groups, R may be selected from the group consisting of a chemical bond, vinyl, allyl, homoallyl, acetal, ester, carboxylic acid, amide, halo-acetamide, thiol, phosphorothiolate monoester, thioester, disulfide, aldehyde, ketone, hydrazide, hydrazine, and amines; as well as those listed in Hermanson (ibid, Hermanson). Where R is intended to be attached to a derivatized biomolecule, R may be selected from the group consisting of a chemical bond, streptavidin, a portion of streptavidin, biotin, phenyl boronic acid, salicylic hydroxamic acid, disulfide, thioester, thiol, phosphorothiolate monoester, hydrazide, hydrazine, amine, acetal, ketone, aldehyde, dialdehyde, bromo- or iodo-acetamide, and esters as well as those listed in Hermanson (Hermanson ibid). Whether R is to be attached to a biomolecule or to a functional group, depending upon the specific moiety for R chosen, the R moiety may either react directly or first require activation before attachment can occur.

Figure 18:
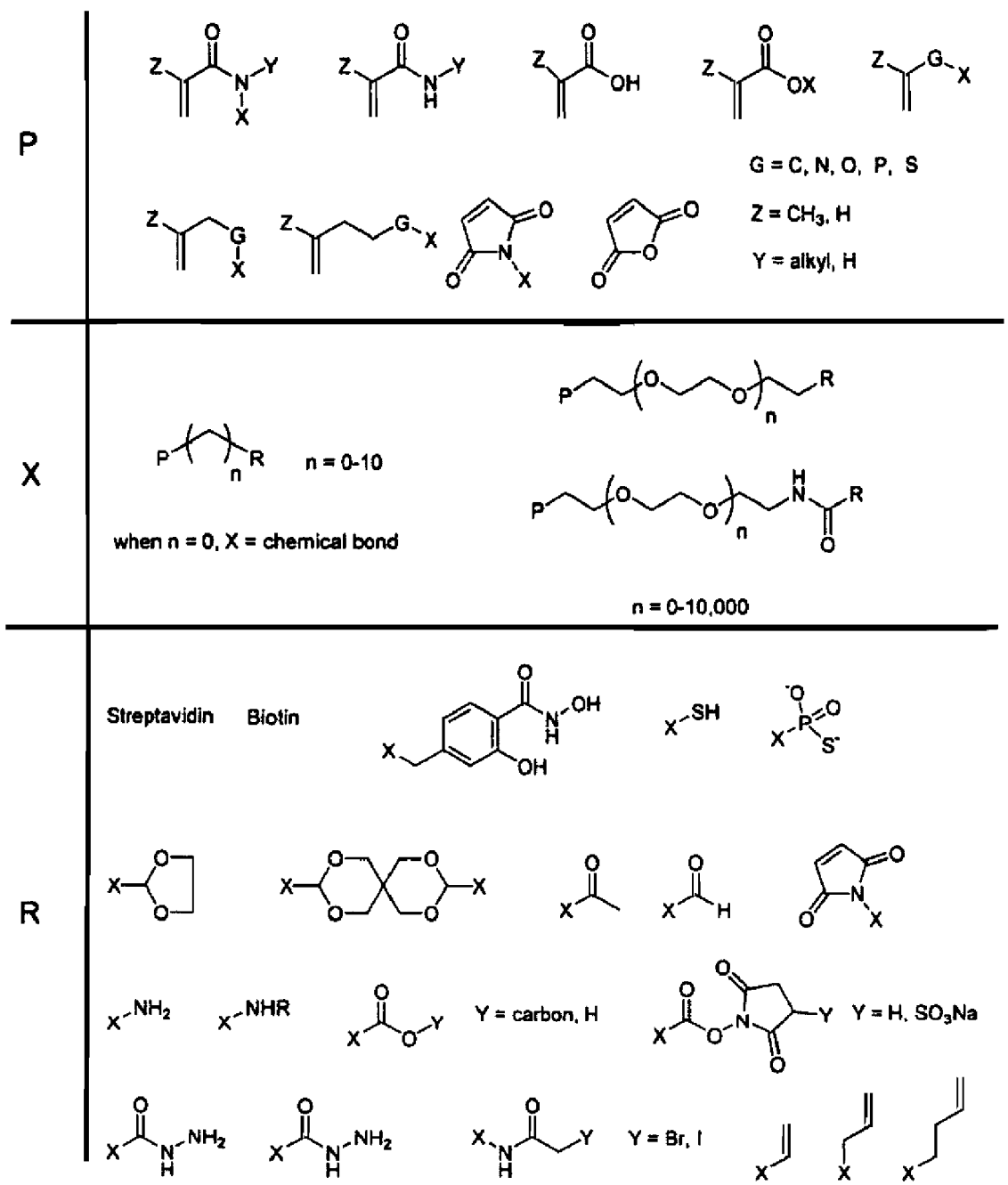
FIG. 18 shows examples of P, X, and R moieties. These may be mixed and matched in any combination.

With respect to the 'A' moiety on the permeation layer polymer backbone, generally, 'A' comprises a reactive center comprising either a carbon atom in the polymer backbone that is sensitive to react in a free radical reaction, or comprises a chemical moiety attached to the polymer backbone, such as tertiary carbons or acetals, that will react either directly, or following sensitization (i.e., activation), become activated wherein activation generally comprises the formation of a species that will participate in a further reaction with a P moiety. For each of P, X, and R, examples are provided in FIG. 18 and Table I.

TABLE I

A Partial List of Functional Moieties Included in Attachment Schemes.

| Structure | Functional Group or Chemical Name | Category |
|---|---|---|
| (acrylate ester structure, CH2=CH-C(=O)-OR) | Acrylate ester | α,β-Unsaturated carbonyl or Ester |
| (acrylic acid structure, CH2=CH-C(=O)-OH) | Acrylic acid | α,β-Unsaturated carbonyl or Acid |
| (acrylamide structure, CH2=CH-C(=O)-NH2) | Acrylamide | α,β-Unsaturated carbonyl or Amide |
| (monosubstituted acrylamide structure, CH2=CH-C(=O)-NHR) | Monosubstituted acrylamide | α,β-Unsaturated carbonyl or Amide |
| (disubstituted acrylamide structure, CH2=CH-C(=O)-NRR1) | Disubstituted acrylamide | α,β-Unsaturated carbonyl or Amide |
| (vinyl structure) R = C, N, O, P, S | Vinyl | Alkene |
| (allyl structure) R = C, N, O, P, S | Allyl | Alkene |
| (homoallyl structure) R = C, N, O, P, S | Homoallyl | Alkene |
| (cyclic anhydride structure, maleic anhydride) | Cyclic anhydride | α,β-Unsaturated carbonyl |
| R–SH | Thiol | Thiol |
| (phosphorothiolate monoester structure) | Phosphorothiolate monoester | Phosphorothiolate |
| (acetal monomer, 1,3-dioxane with R) | Acetal monomer | Acetal |

TABLE I-continued

A Partial List of Functional Moieties Included in Attachment Schemes.

| Structure | Functional Group or Chemical Name | Category |
|---|---|---|
| (acetal dimer, spiro bis-dioxane with two R groups) | Acetal dimer | Acetal |
| (ketone, R-C(=O)-R1) | Ketone | Carbonyl |
| (aldehyde, R-C(=O)-H) | Aldehyde | Carbonyl |
| (hydrazide, R-C(=O)-NH-NH2) | Hydrazide | Hydrazide |
| (hydrazine, R-CH2-NH-NH2) | Hydrazine | Hydrazine |
| (amide, R-NH-C(=O)-R1) | Amide | Amide |
| X–NH2 | Primary amine | Amine |
| X–NHR | Substituted amine | Amine |
| (ester, R-C(=O)-O-R1) | Ester | Ester |
| (bromo- or iodo-acetamide, R-NH-C(=O)-CH2-Y) Y = Br, I | Bromo- or Iodo-acetamide | Haloacetamide |
| (thioester, R-S-C(=O)-R1) | Thioester | Thioester |
| (disulfide, R-S-S-R1) | disulfide | Disulfide |
| (sulfonated-N-hydroxy succinimidyl ester structure) Y = H, $SO_3Na$ | (sulfonated)-N-Hydroxy succinimidyl ester | Ester |
| (ether, -CH2-O-CH2-) | Ether | Ether |
| (alkyl chain of seven carbons) | Alkyl chain of seven carbons | Alkyl Chain |

TABLE I-continued

A Partial List of Functional Moieties Included in Attachment Schemes.

| Structure | Functional Group or Chemical Name | Category |
|---|---|---|
| (epoxide structure) | Epoxide | Epoxide |

The chemistry of attaching functional groups and derivatized biomolecules can vary depending upon the nature of each moiety chosen. In some cases, in order for an 'A' or R to react and participate in bonding to a P or a derivatized biomolecule, only direct contact with the moiety to which bonding is to occur need take place. For example, if 'A' or R comprises an ester, the derivatized biomolecule only need include a hydrazide moiety. Moieties not requiring activation for bonding include aldehyde, ketone, amine, hydrazine, hydrazide, haloacetamide, thiol, phosphorothiolate monoester, and ester. Each of these may be paired for reaction in the following combinations shown in Table II.

TABLE II

| 'A' or R constituent | Moiety associated with P or derivative of biomolecule |
|---|---|
| Aldehyde, ketone, ester | Amine, hydrazide, hydrazine |
| Iodo or bromoacetamides | Thiols phosphorothiolate monoester, |
| Salicylic hydroxamic acid | Phenyl boronic acid |
| Streptavidin | Biotin |

In other cases, 'A', R, P, or the derivatized portion of the biomolecule must be activated for bonding or attachment to occur. In this case chemical moieties may comprise any of disulfide, thioester, tertiary carbon, alkene, alkyl ether, acetal, and carboxylic acid, Such moieties requiring activation may be paired as shown in Table III

TABLE III

| 'A' or R constituent | Moiety associated with P or derivative of biomolecule |
|---|---|
| Acetal | Amine, hydrazide, hydrazine |
| Thioester, disulfide | Halo-acetamide |
| Alkene | Alkene, tertiary alkane |
| Tertiary carbon | Alkene |
| Alkyl ether | Alkene |
| Carboxylic acid | Amines, hydrazides, hydrazine |
| Epoxide | Alcohol |

Whether attachment is carried out using moieties requiring prior activation (whether 'A' R, P or a derivatized biomolecule) or not, the attachment may comprise either covalent or noncovalent bonding. Where no activation is required for attachment of either functional groups or derivatized molecules, reactive moieties present on the permeation layer of the entire microarray are subject to participation in the attachment reaction. This allows the incorporation of high densities of R moieties of functional groups for further attachment of biomolecules onto any portion of the array.

Where activation is required for attachment to occur, the moieties may be either specifically or nonspecifically activated. Nonspecific activation, generally allows activation of moieties requiring activation present on the permeation layer of the entire microarray. Specific activation on the other hand provides for the activation of only selected moieties requiring activation present on the array. In a preferred embodiment, specific activation is carried out by applying an electronic potential (either positive or negative) to preselected electrodes of the array so that the charge generated will directly influence the pH of a solution, such as a solution overlying the microarray, directly above the electrode. In this manner, the moieties requiring activation (A or R) undergo a chemical transformation and become available for attachment to a moiety, e.g., a reactive center of a P, an R, or to a derivatized biomolecule. This specific activation provides a high degree of versatility to the invention in that specific capture sites of the array may be provided high densities of binding capacity for biomolecules on an "on-demand" basis.

Attachment chemistry of the invention further comprises novel grafting methods wherein functional groups are incorporated onto the permeation layer using the various attachment chemistries noted above in conjunction with such grafting methods. In one embodiment, grafting is carried out in a slurry method. In another embodiment, grafting is carried out in a solution method. Whether by slurry or solution, the functional groups may be incorporated across the entire array or only at preselected locations. For embodiments which contemplate attachment across the entire array, generally, 'A' and/or R moieties may or may not require prior activation. For embodiments which contemplate attachment only at preselected locations, generally, 'A' and/or R moieties require activation prior to attachment.

Attachment chemistry used in the grafting methods of the invention further contemplates employing the use of either previously polymerized functional groups or the use of reaction conditions that allow for the polymerization of the functional groups during attachment. In either case grafting implies that the functional groups are attached to a preformed base permeation layer having either 'A' or R moieties wherein the 'A' moieties are reactive centers of the permeation layer and the R moieties are present either from 'copolymerization' of individual P—X—R functional groups, or are present from the prior grafting of functional groups either in the form of individual P—X—R groups, previously polymerized P—X—R groups, or P—X—R groups polymerized simultaneously with grafting.

The attachment of functional groups during formation of the permeation layer onto the microarray by polymerizing a group of monomers with different chemical structures is designated 'copolymerization'. In this embodiment a reactive center of P becomes attached to a reactive center of the permeation layer polymer during formation of the permeation layer onto the microarray. The reactive P may either be already incorporated into a polymerized functional group or may participate in simultaneous polymerization of the functional group as it is attached to the permeation layer matrix. Generally, attachment via copolymerization uses nonspecific attachment chemistry and the functional groups which are incorporated into the permeation layer are attached throughout the entire array.

Attachment of functional groups onto a preformed permeation layer is designated 'grafting'. In one preferred embodiment, grafting is carried out using slurry grafting. In this method, functional groups having the formula P—X—R are contacted with a permeation layer in a concentrated slurry with an initiator molecule that upon being induced to react initiates both (1) bonding between reactive centers of the permeation layer (i.e., either 'A' or an R) and reactive centers of the P moiety, and (2) polymerization of the functional group through a reactive center on the P moiety. Where the functional group has been previously polymerized, the grafting process primarily only concerns the attachment of the previously polymerized groups to the permeation layer. Details of the slurry grafting method are provided in Example 2 below. In a preferred embodiment of this method, the functional groups and initiator are only partially in solution.

In another preferred embodiment, grafting may be carried out using solution grafting. In this method, functional groups having the formula P—X—R are contacted with a permeation layer in a solution with an initiator molecule that upon being induced to react initiates both (1) bonding between reactive centers of the permeation layer (i.e., either 'A' or an R) and reactive centers of the P moiety, and (2) polymerization of the functional group through a reactive center on the P moiety. Where the functional group has been previously polymerized, the grafting process primarily only concerns the attachment of the previously polymerized groups to the permeation layer. Details of the solution grafting method are provided in Example 3 below. In a preferred embodiment of this method, the functional groups and initiator are completely dissolved in solution.

Figure 19:
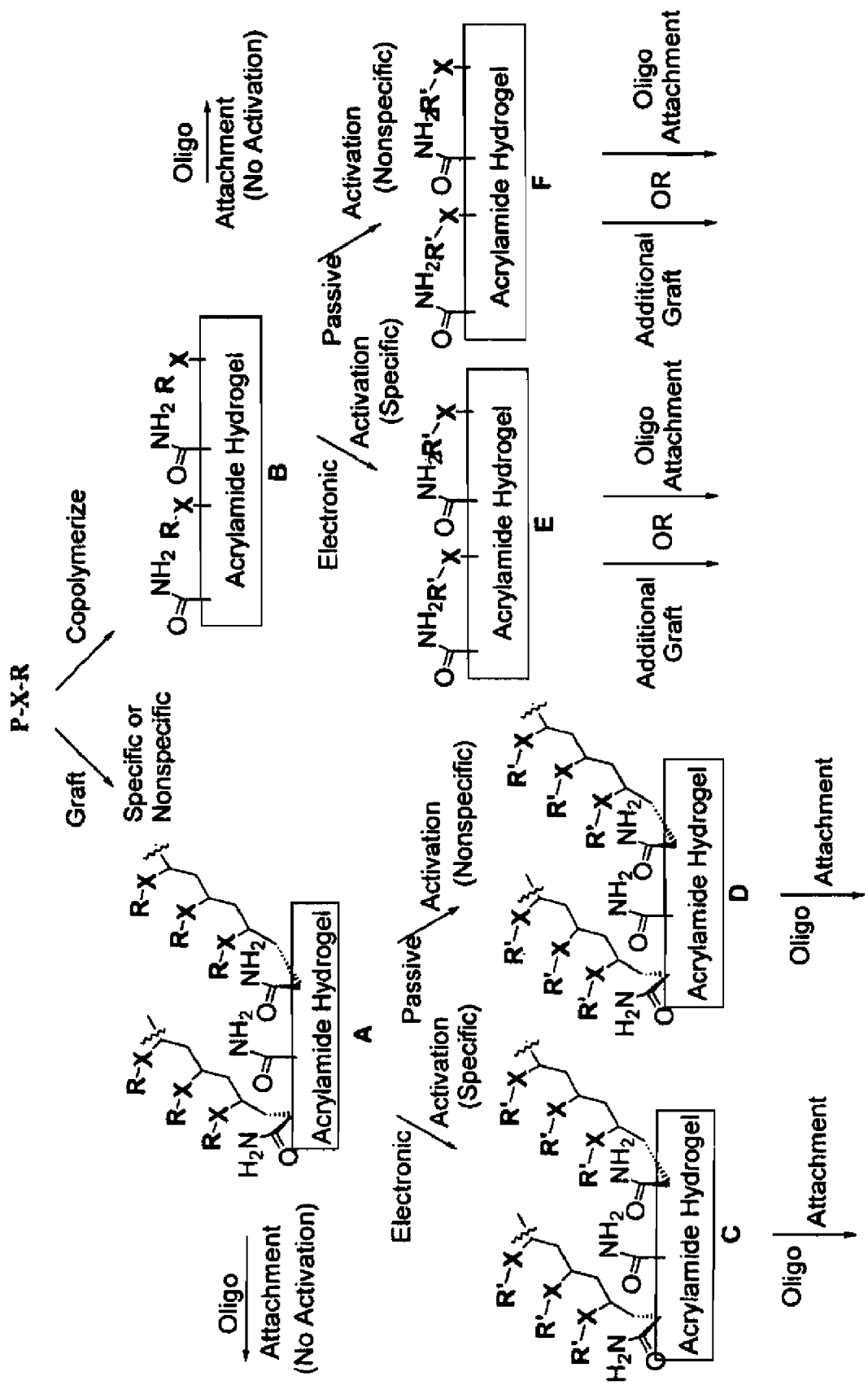
FIGS. 19 and 20 show schematic diagrams of various permutations of adding P—X—R groups to permeation layers.
Figure 20:
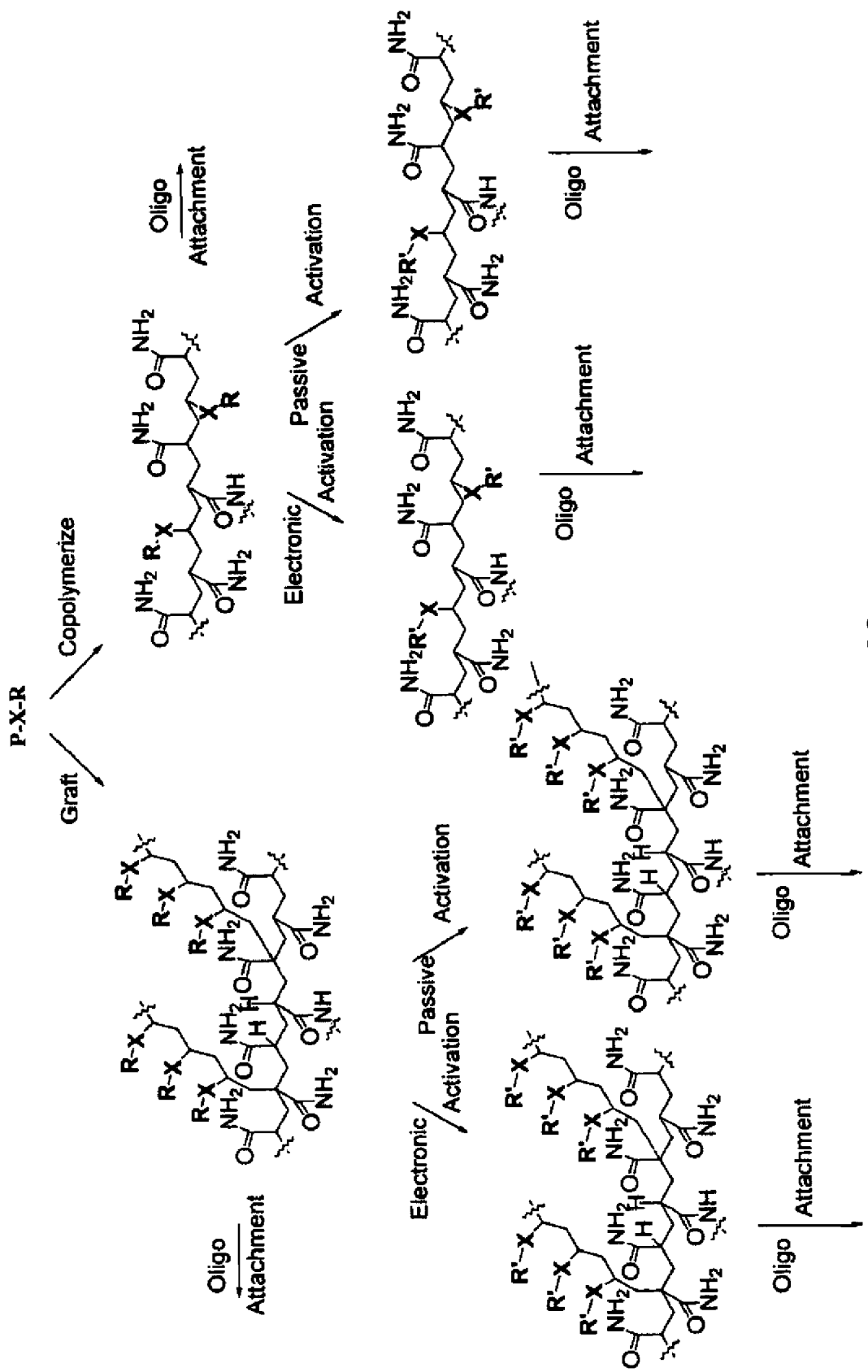

Whether slurry or solution grafting is used, the method of the invention allows the versatility of carrying out the grafting in either a nonspecific or a specific format. Where a nonspecific format is used, the 'A', and/or R moieties may comprise those that require activation. For those moieties that require activation, grafting can be applied across the entire array by altering pH conditions of the overlying solution. Where specific activation is contemplated during grafting, grafting may be directed to occur only above the electrodes of the microarray by using 'A' and/or R moieties that require activation in conjunction with use of the initiator and functional groups. FIGS. 19 and 20 show various configurations of bonding multiples of R moieties for attaching biomolecules. FIG. 20 is more detailed in that it shows chemical structures of the permeation layer. FIG. 19 shows various permutations of added P—X—R groups. In "A", P—X—R groups have been polymerized in a grafting reaction to a permeation layer. The grafting may be either nonspecific or specific. The diagram depicts specific in that some reactive centers of the permeation layer may be kept from grafting. Once such grafting has occurred, derivatized biomolecules may be attached directly without activation, if an R moiety that does not require activation is present, or the R moiety may be further activated for attaching biomolecules in either a nonspecific or specific mode as indicated in "C" and "D", where an R moiety requiring activation is present. In "B", P—X—R groups are indicated as being copolymerized into the permeation layer individually after which they may be directly attached to derivatized biomolecules as stated above, or activated, assuming the appropriate R moiety is present, in a nonspecific or specific manner for further attachment of either additional P—X—R groups or derivatized biomolecules.

Attachment of the grafted monomer to achieve covalent linkage may be initiated by any number of methods. For example, grafting may use thermal decomposition of initiators (e.g. AIBN, benzoyl peroxide), photolytic cleavage of initiators (e.g. UV initiation of a mixture of 50% 2,4,6-trimethylbenzoyl-diphenyl-phosphineoxide and 50% 2-hydroxy-2-methyl-1-phenyl-propan-1-one (Daracur 4265, Ciba-Speciality Chemicals C; Tarrytown N.Y.) (hereinafter referred to as D 4265), redox reactions (e.g. cerium (IV) sulphate), ionizing radiation (e.g. ($\alpha$, $\beta$, $\gamma$ or X-rays), plasma initiation (e.g. Argon, Nitrogen, Oxygen), or electrolytic initiation using tetrabutylammonium perchlorate in which the grafting occurs only over a preselected site using an electric current (Samal, S. K.; Nayak, B. *J. Polym. Sci. Polym. Chem. Ed* 1988, 21, 1035, herein incorporated by reference). Moreover, the grafting process may also be specifically directed to predetermined locations of the array by using chemical moieties that must be activated prior to reaction.

In yet another embodiment, specificity of attachment may occur by employing properties of the initiator used to initiate polymerization and grafting or by electrochemical activation. Generally, the initiator is induced to become reactive by contact with either heat or radiation. In his embodiment, whether also in conjunction with 'A' or R moieties that require activation, grafting using either slurry or solution methods may be specifically directed to predetermined locations on the array by masking contact of the radiation to only preselected locations of the array. Another method of specific activation is to bias electrodes under conditions which generate free radicals in electrochemically designed initiators.

To further clarify aspects of the invention, the following descriptions of various aspects of attachment chemistry are detailed below.

In one embodiment, the functional group P—X—R in a polymerization grafting reaction is attached to 'A' of the permeation layer. This can be diagramed as follows wherein X is a chemical bond:

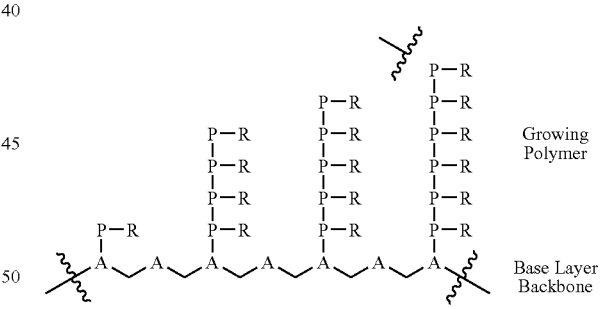

An example of a chemical reaction of this diagram is:

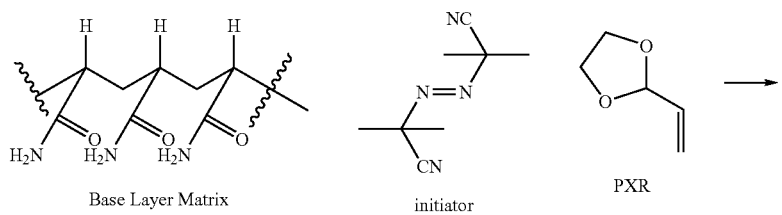

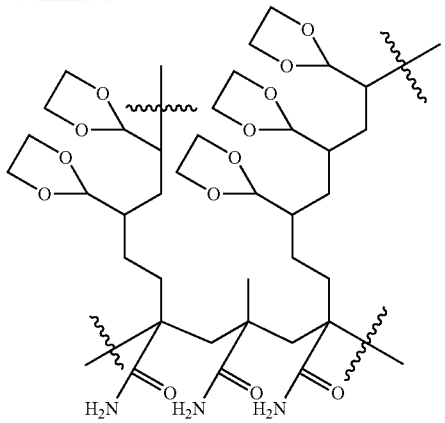

Resultant Structure

In another embodiment, functional groups are copolymerized or chemically linked into the permeation layer matrix through an 'A' moiety and are available for further polymerization grafting through the R moiety. In the diagram shown X is not a simple chemical bond.

ation layer. Here the result can be diagramed as follows wherein X' in the polymerizing functional group is a chemical bond:

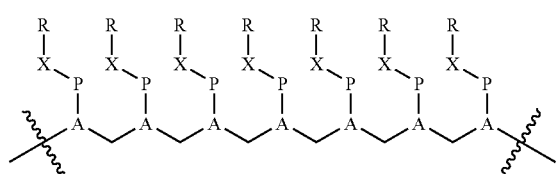

Permeation Base Layer

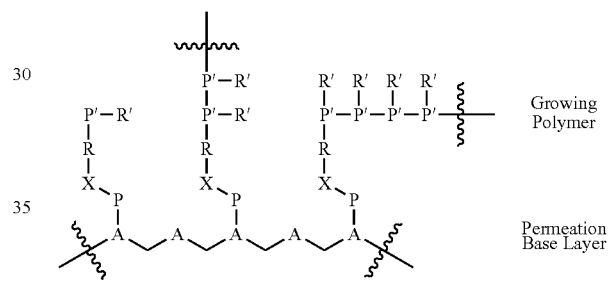

In a further embodiment, additional P'-X'-R' groups may polymerize onto an R moiety (whether or not R requires activation) of the functional group that was previously bound (either during copolymerization or grafting) to the permeation layer.

An example of a chemical reaction for the above diagram wherein R comprises a moiety that must first be activated is:

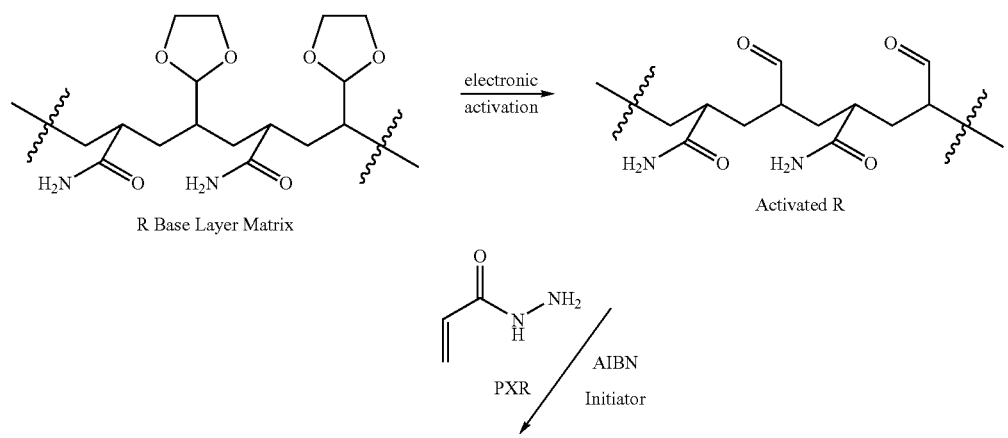

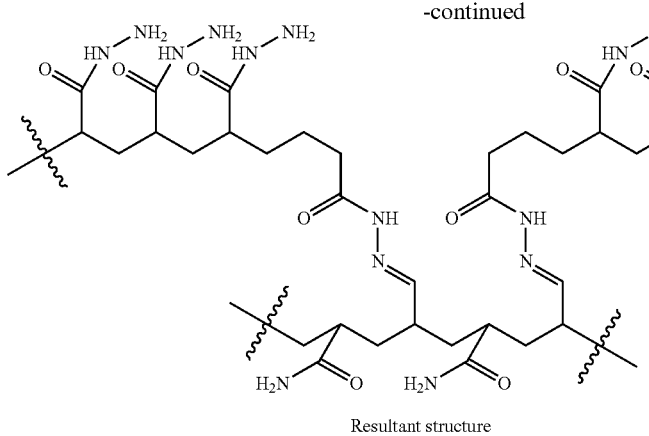

Resultant structure

Polymeric expansion may continue for many additions forming long chains of polymer containing large numbers of R moieties available for binding biomolecules, designated Z-bio in the following diagram:

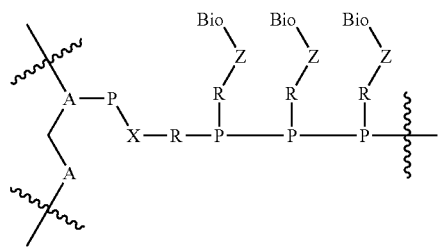

Figure 21:
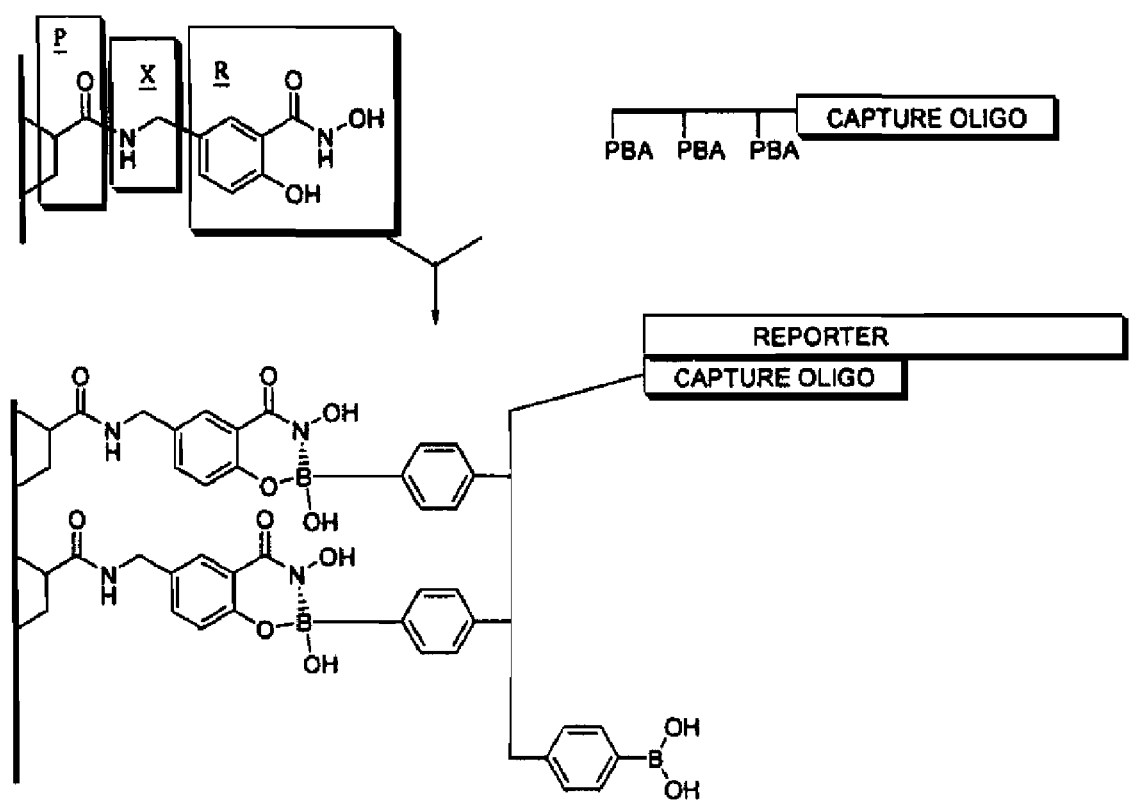
FIG. 21 shows one form of attachment chemistry of a functional group of the formula P—X—R wherein methacrylamide is P, X is a chemical bond, and R is SHA. The SHA moiety attaches to PBA labeled oligomer biomolecule.

In a preferred embodiment, Z, the derivative attached to the biomolecule is preferably selected from the group consisting of a chemical bond, streptavidin, biotin, phenyl boronic acid, salicylic hydroxamic acid, thiol, phosphorothiolate monoester, hydrazide, hydrazine, amine, ketone, aldehyde, dialdehyde, bromo- or iodo-acetamide, and esters as well as those derivatives listed in Hermanson (Hermanson ibid.). In one embodiment, the derivatized moiety may attach to several R moieties. Such a situation is diagramed in FIG. 21 wherein PBA moieties attach to SHA moieties individually comprising R moieties.

An example of polymerization during grafting can be diagramed as follows:

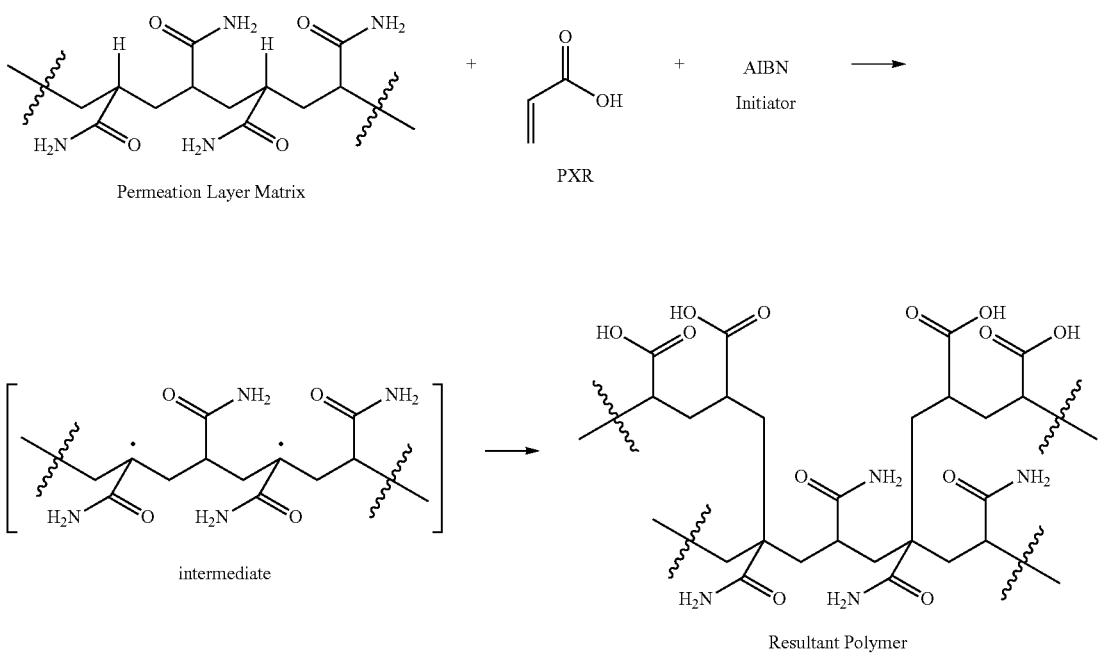

Wherein P is the reactive double bond moiety of the monomer, X is a chemical bond between the alkene and carbonyl carbon, and R is the carboxy group used to attach to a biomolecule. The initiator, when heated above 70° C., extrudes nitrogen gas generating two radical species which abstract hydrogen from the permeation layer. This radical backbone then reacts with the double bond of the monomer to form a covalent bond between the backbone and the monomer and also generates a tertiary radical within the newly bonded monomer. This radical can continue the polymerization reaction resulting in a polymeric backbone.

Figure 22A:
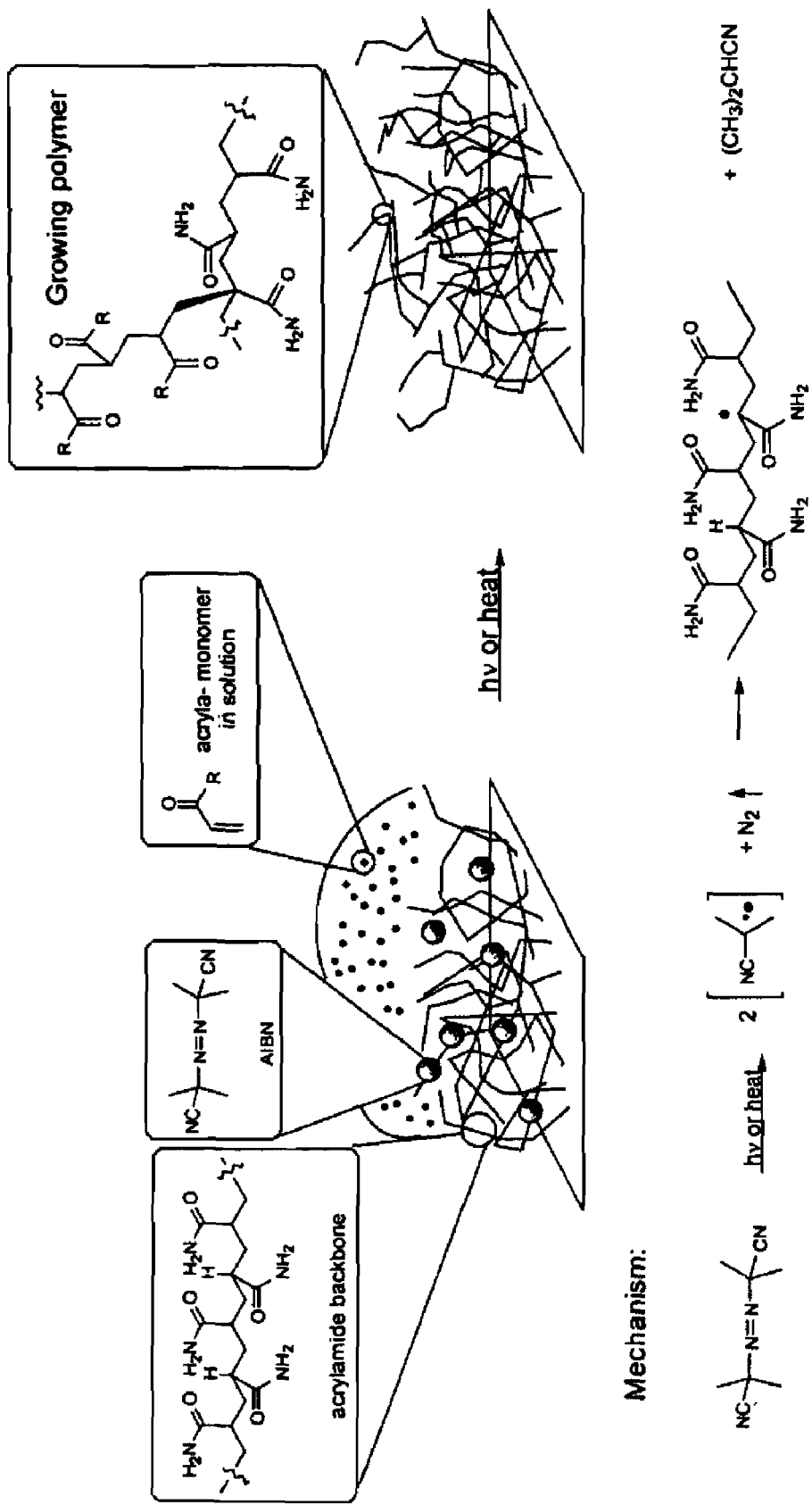
FIG. 22A shows a schematic for slurry grafting wherein the initiator AIBN precipitates from solution onto the base layer while the functional group comprising a methacrylamide monomer co-precipitates and also remains in part in solution above the surface. Either heat and or UV radiation are employed to react AIBN forming reactive free radicals. The free radical scavenges hydrogen from the base permeation layer matrix providing an attachment site for polymer.
Figure 22B:
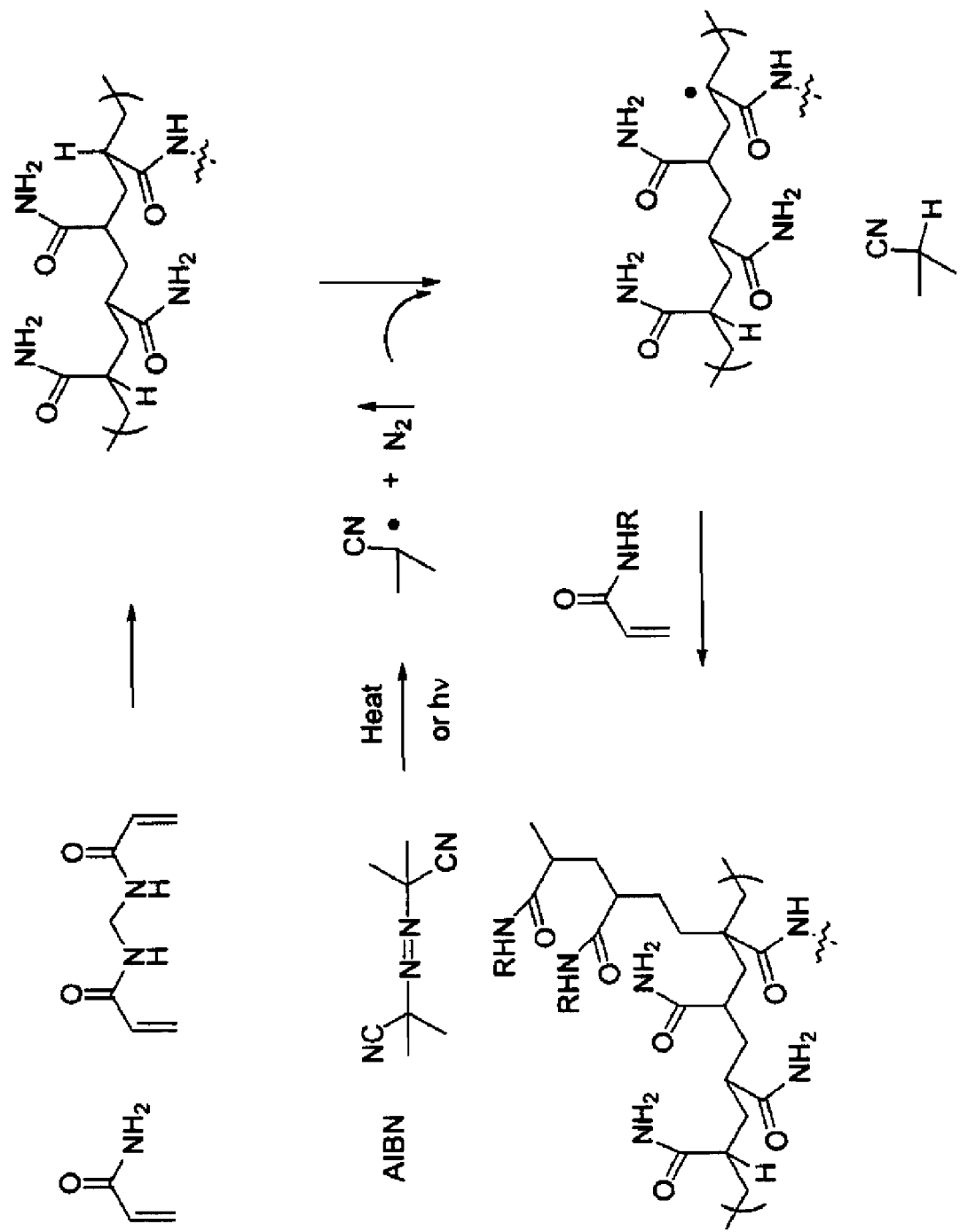
FIG. 22B shows details of the chemical mechanism for the process shown in FIG. 22A.
Figure 23:
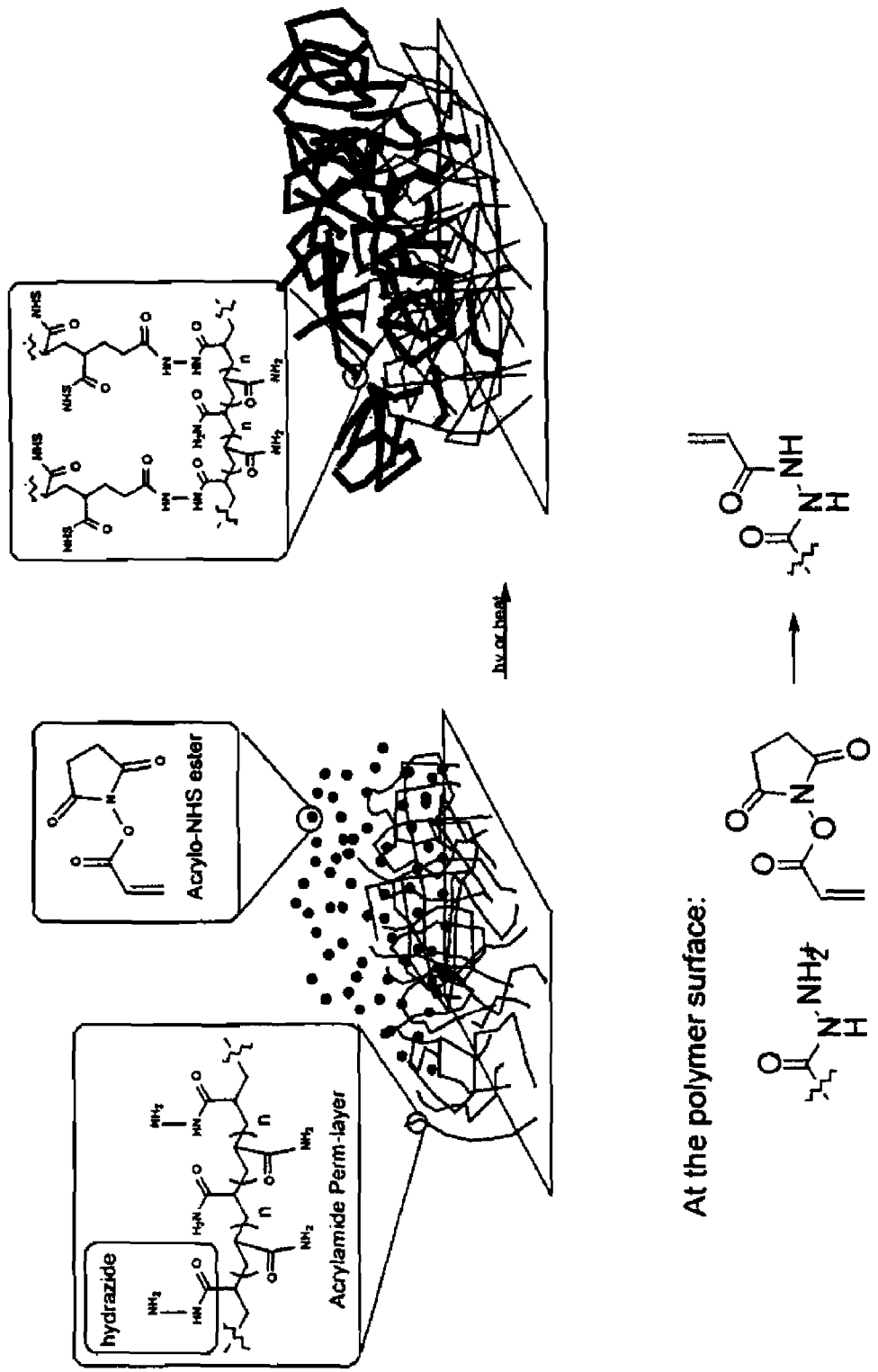
FIG. 23 shows an embodiment of the invention wherein a nucleophilic hydrazide modified base permeation layer is exposed to an acryloyl-NHS ester, a strong electrophile. Upon reaction, the acryloyl group will be fixed to the permeation layer and polymerized.

The reaction described above may be initiated either non-electronically, wherein the polymer is spread over the surface of the permeation layer, or electronically using an initiator which is activated from biasing of the electrodes resulting in high density specific placement of the polymer at specified capture sites of the array. When the reaction is carried out in the presence of a base permeation layer containing reactive moieties that can participate as sites of attachment for the growing polymer in the polymerization reaction, the result is an array that comprises a growing or polymerizing mass of polymer chains on the surface of the array either across the entire array or at specified locations. FIGS. 22A and B and 23 are diagrams representing grafting polymerization using either an acrylamide P—X—R group (FIG. 22B) or an acrylic-NHS ester (FIG. 23). FIG. 22B shows a more detailed mechanism for what is depicted in FIG. 22A. In either case, as depicted, a polymerizing mass is formed on the surface of the permeation layer. As with other embodiments of the invention, this growing polymerizing reaction can be nonspecifically or specifically directed.

In the following examples are disclosed various experiments wherein functional groups are added to the permeation layer of an electronically addressable microarray. In Example 1 is shown attachment chemistry of prior art wherein biomolecule attachment levels are limited with respect to that of the current invention. This example also shows that attachment moieties of the current invention employed as P—X—R groups provide attachment of biomolecules to levels at least equivalent to prior attachment chemistry methods. Example 2 shows three attachment schemes wherein the grafting method developed for the current invention involves a "slurry" method. Example 3 shows solution grafting for the attachment of functional groups to the permeation layer. Example 4 provides experiments proving the utility of a "plasma graft" method. Example 5 provides three experiments wherein a permeation layer is formed that has reactive centers R which require activation prior to attachment. Additionally, the example proves the ability to carry out specific attachment using electronic biasing so bonding of the functional group occurs only at capture sites of the array. Example 6 shows reactive centers R which comprise a moiety that must be activated prior to attachment of derivatized biomolecules.

EXAMPLE 1

Attachment chemistry typically used in the prior art is limited by the number of available reactive sites on the substrate surface. For every reactive site, only one moiety may be attached for binding a molecular structure that is involved in detection of a target species within a sample. For example, for every reactive moiety on the substrate, only one detection probe may be bound.

In order to show that some of the chemical moieties used in attachment chemistry of the present invention would function at least to the levels of equivalent chemistry known in the prior art, three experiments were carried out wherein chemical groups for attaching biomolecules were placed on a microarray and processed without polymerization. The resulting binding was due only to the individual available sites on the array.

a) Experiment 1

Attachment of Cyanomethyl Protected Salicylic Hydroxamic Acid Pentyl Maleimide (SA(OCM)-X-Mal)

Microarrays that were layered with a base hydrogel permeation layer comprising 9:0.5:0.5 acrylamide/methylene bis acrylamide/N,N'-bis(acryloyl)cystamine and D 4265 as UV initiator were reacted with a maleimide linker to form an attachment matrix above the permeation layer. Specifically, the arrays were incubated in 10 ml of bond of N,N'-bis(acryloyl)cystamine. The arrays were washed three times with 50 mM sodium acetate pH 6.0. Next, a solution of 8.5 mg of SA(OCM)-X-Mal in 2 ml DMF were added to 20 ml sodium acetate pH 6.0 and the arrays were incubated in the acetate solution for 45 minutes. This was followed by addition of 1 M $NH_2OH$ (in 0.1 M $NaHCO_3$, pH 8.5) and allowed to react for 3 hours followed by extensive washing of the arrays in water.

Figure 1B:
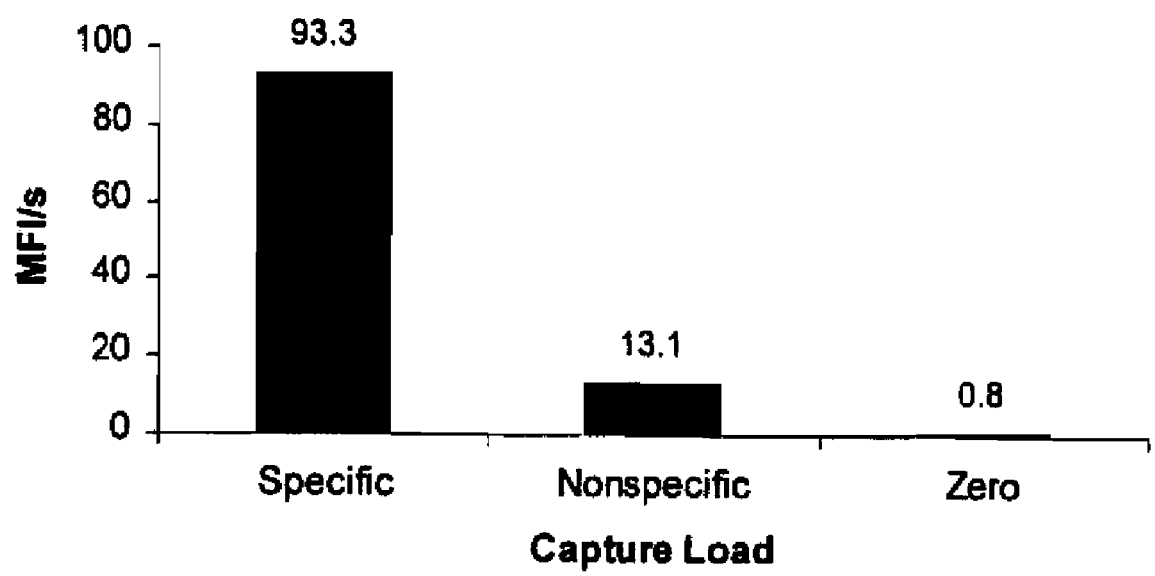
FIG. 1B is a bar graph showing the relative difference between specific and nonspecific binding in MFI/s. This level corresponds to a density of binding of $1 \times 10^7$.

Binding assays were conducted using electronic addressing of a T12 probe labeled with multiple PBAs, a specific attachment moiety, and a Bodipy Texas Red fluorescent dye ($PBA_n$-T12-BTR, where n is a number between 1 and 8) (50 nm in 50 mM histidine buffer at 400 na/capture site for 2 minutes). T12-BTR was used as a nonspecific control and addressed under the same conditions. As shown in FIG. 1A the capture sites (columns 2 and 4) to which the PBA labeled probes were addressed exhibited specific binding. Very low levels of nonspecific binding were observed in columns 3 and 5. FIG. 1B shows a bar graph of the average of the results in FIG. 1A. The overall levels of binding shown correlate to a range of $5 \times 10^7$ molecules per pad. Such levels are comparable to known prior art attachment chemistry.

b) Experiment 2

Attachment of N-propyl-bromoacetamide(SA(OCM)-X-BrAc)

Figure 24A:
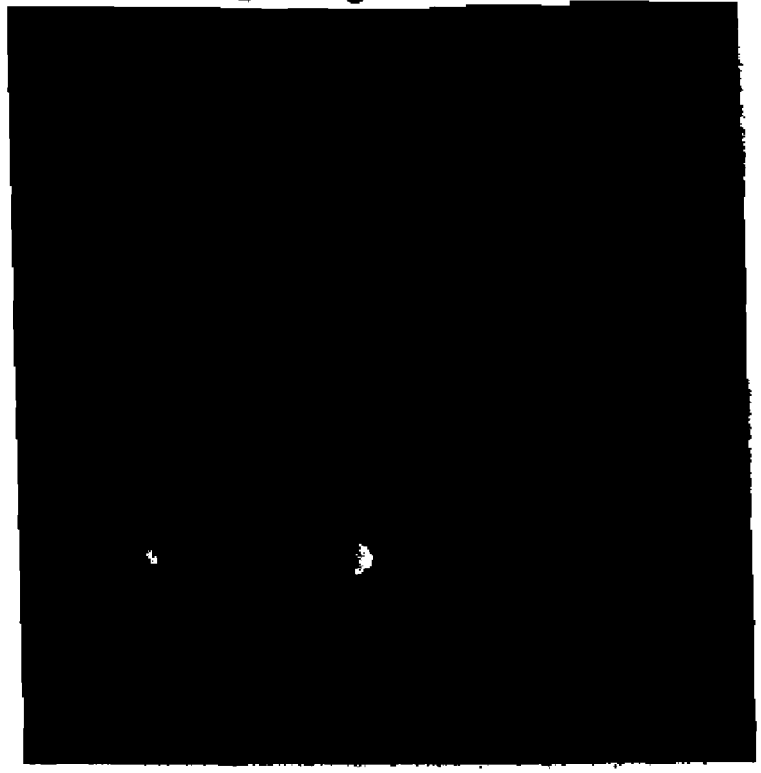
FIGS. 24A and B show results of probe attachment density following attachment of SHA via a bromoacetamide linkage as a method described in the prior art.
Figure 24B:
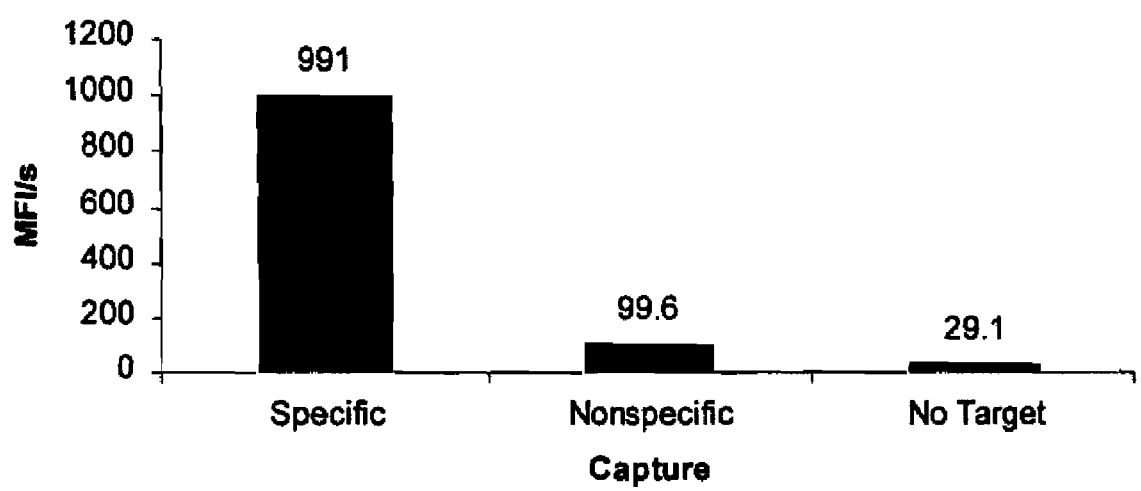
FIG. 24B shows the relative intensities of specific and non specific binding.

Microarrays which contained a base permeation layer as described in experiment 1 tris-HCl pH 8.2 under nitrogen for 1 hour. The arrays were then washed three times with 50 mM sodium acetate, pH 6.0. The microarray was treated with a solution containing 0.40 mL of a solution from a 1.0 mL solution containing 11.0 mg of SA(OCM)-X—BrAc diluted into 5.0 mL Tris-HCl at pH=8 and incubated for 3 h. The $NaHCO_3$, and again washed with copious amounts of water. Electronic binding of BTR was used as a nonspecific target and addressed under the same conditions. After addressing the chips were subjected to the standard washing protocol. As shown in FIG. 24A the specific capture sites (columns 1 and 3) to which the PBA labeled probes were addressed exhibited specific binding. Very low levels of nonspecific binding were observed in columns 2 and 4. FIG. 24A shows a bar graph of the average of the results in FIG. 24A. The overall levels of binding are in the range of $5 \times 10^7$ fluorophores/5000 $\mu m^2$ pad. Such levels are comparable to known prior art attachment chemistry.

c) Experiment 3

Attachment of Cyanomethyl Protected Salicylic Hydroxamic Acid NHS Ester (SA(OCM)-X—NHS Microarrays which contained a base permeation layer as described in experiment 1 above were modified to contain primary amines. The arrays were incubated with 10 ml of 20 mM DTT in 0.5 M tris-HCl ph 8.2 under nitrogen for 1 hour. Next, 8 µl of 0.5 M 3-bromopropylamine were added under nitrogen for 2 hours at 37° C. This was followed by addition of 9 µl of 2 M DTT in 0.5 M tris-HCl and incubated for 30 minutes followed by washing with water. The arrays were then rinsed with dry DMF and then overlayed with 80 µl of 25 mM SAOCM-X—NHS in dry DMF. Triethylamine (8 µl) was added and the arrays were incubated at room temperature for 2.5 hours. The arrays were then washed 3 times with dry DMF and 3 times with water. Finally, 1M NH$_2$OH (in 0.1M NaHCO$_3$, pH 8.5) was overlayed for 3 hours followed by washing the chips in water.

Figure 3A:
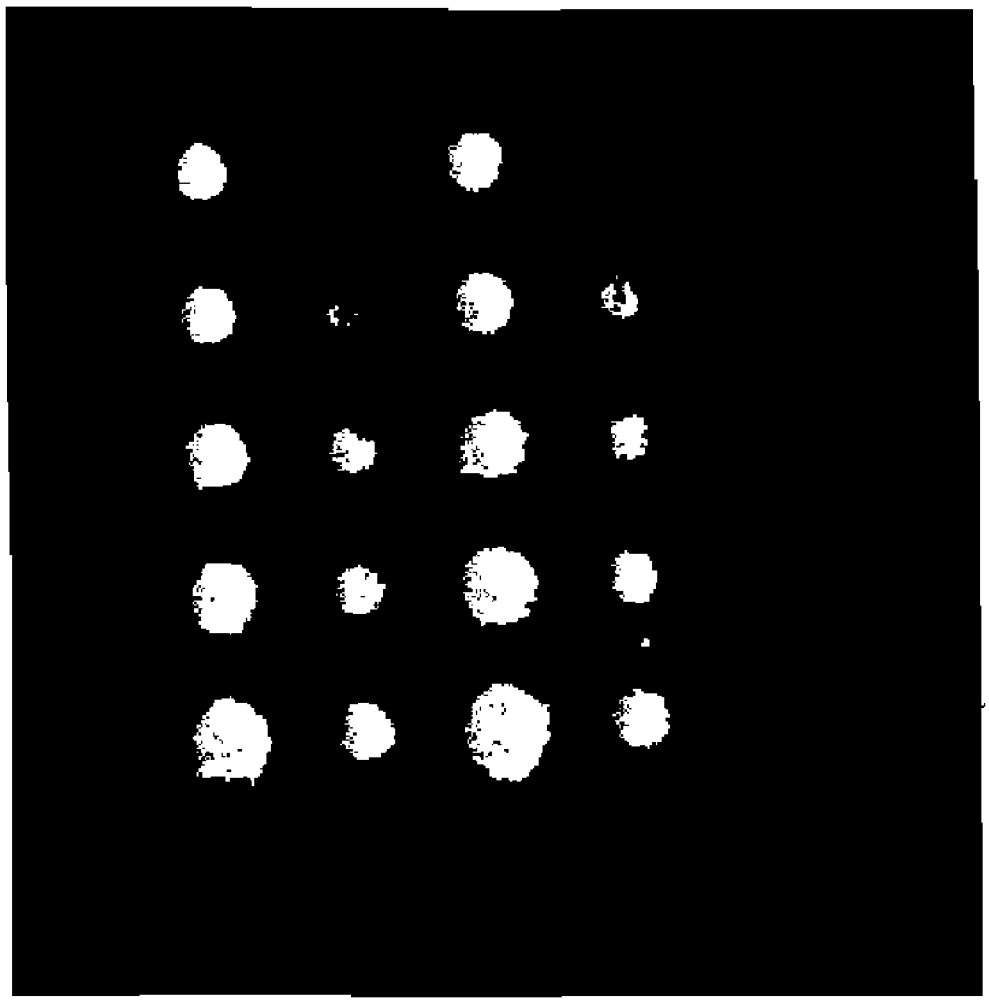
FIGS. 3A and B show results of probe attachment density following polymerization of acrylate ester with a tethered amine, or an amine ester.
Figure 3B:
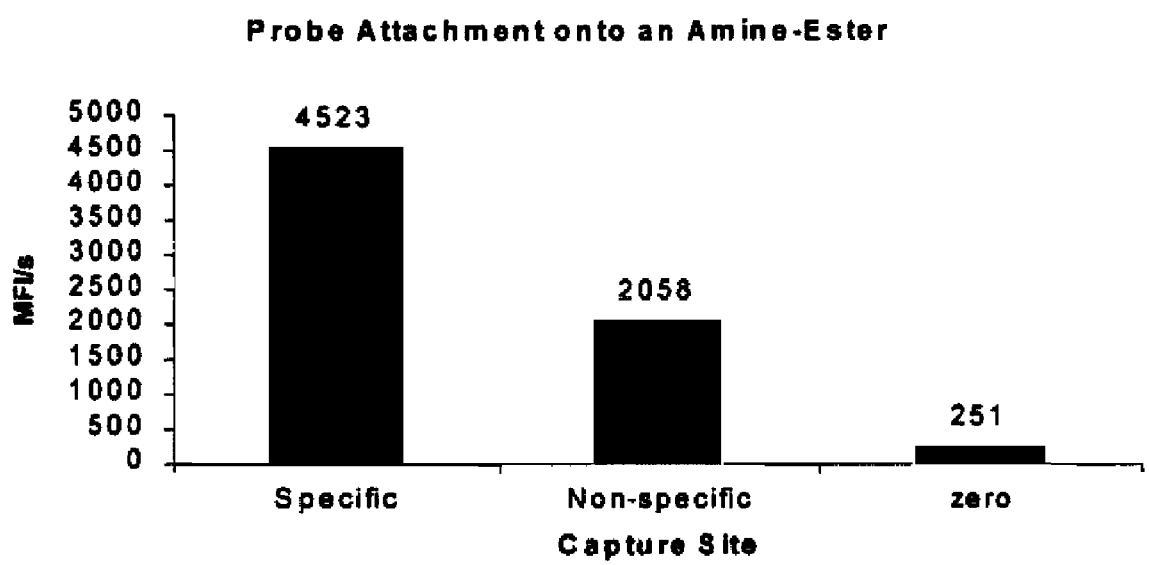
FIG. 3B shows the relative intensities of specific and nonspecific binding. The intensities increase from rows 1 to 5 due to a light intensity gradient increasing from row 1 to row 5.

Binding assays were conducted by electronic addressing of PBA-T12-BTR (50 nm) in 50 mM histidine buffer using 400 nA/site for 2 minutes. T12-BTR was used as a nonspecific control and addressed under the same conditions. After addressing the probes, the arrays were subjected to washing in STE as described above. FIG. 3A shows the attachment results wherein specific binding (columns 1 and 3) were strong while nonspecific binding (columns 2 and 4) was distinctly lower. FIG. 3B shows a bar graph of the ratio between specific and nonspecific binding wherein the levels are comparable to typical attachment chemistry.

Thus, from the above experiments, we have shown that chemical attachment moieties may be bound to the reactive centers of the permeation layer of the electronically addressable microarray of the invention. Moreover, such attachment is comparable to existing attachment technology. Since attachment chemistry moieties we desire to attach using the methods of the current invention are functional, we further tested their attachment using grafting methods and specific and nonspecific activation of the invention.

EXAMPLE 2

In this experiment, chemical moieties for attaching biomolecules at specific locations on the microarray are grafted onto preformed permeation layers. In one embodiment, the grafting method developed for the current invention involves a "slurry" method. This method achieves a high density of grafted activation moieties (e.g., substituted acrylamide or methacrylamide monomer) onto acrylamide-based hydrogel permeation layers. In this method, a high concentration of thermally activated initiator is used to obtain grafting onto the preformed permeation layer.

In a preferred embodiment a slurry is made of polymerization initiator and attachment monomer which are both only slightly soluble at room temperature. The slurry is applied to the base permeation layer of a microarray where the initiator and particulates of the monomer settle onto the surface of the preformed polymer layer. The temperature is then raised to both activate the initiator and dissolve the particulates which results in a high concentration of initiator radicals and dissolved monomer locally near the surface of the preformed polymer layer. Attachment of the monomer (i.e., grafting) and polymerization of the monomer occur simultaneously, resulting in covalent attachment of polymerized functional group to the permeation layer. In this manner, the biomolecule attachment moieties (i.e., R moieties) are segregated mainly to the upper region of the polymer layer and consequently are isolated from any deleterious effects that may be caused by electrolysis products of the underlying electrodes or direct electrochemical oxidation at the electrodes.

In comparison to systems which have the attachment sites originating only from the available sites on the substrate layer, the grafted system of the current invention significantly increases the density of sites for attaching biomolecules and consequently allows for a decreased background due to nonspecific binding.

Experiments for Example 2 a) Experiment 1

A base hydrogel permeation layer was formed on an electronically addressable microarray comprising acrylamide cross linked with methylene-bisacrylamide. Prior to formation of the base layer, the underlying substrate was extensively cleaned using an argon plasma. The base layer was laid down using UV polymerization (90% acrylamide, 10% bis, DMSO/H$_2$O (50/50 v/v), UV initiation with 0.3 mg/ml D 4265). Following formation, the arrays were dried at 70° C. for 15 minutes, rinsed with water, and dried a second time.

The attachment layer was grafted using methacrylamide-SHA (Meth-SHA) (15 mg/ml) and AIBN (30 mg/ml) in 10 ml 20% DMSO/80% H$_2$O. The arrays were contacted with this mixture for 1 hour at 80° C. followed by rinsing with DMSO and water. A control array was produced wherein no SHA was present using the same reaction conditions. Table IV provides the mole % of Meth-SHA and AIBN. Also listed are probe densities obtained following exposure of the grafted microarray to 10 µM PBA-ATA5-BTR for 10 minutes.

TABLE IV

| Array | moles of SHA | [SHA] (M) | moles of AIBN | [AIBN] (M) | mole % SHA | mole % AIBN | probe density |
|---|---|---|---|---|---|---|---|
| test | $2.99 \times 10^{-4}$ | 0.02 | $1.83 \times 10^{-3}$ | 0.18 | 14 | 86 | $6.64 \times 10^7 +/- 4.3 \times 10^6$ |
| control | 0 | 0 | $1.83 \times 10^{-3}$ | 0.18 | 0 | 100 | $7.62 \times 10^5 +/- 1.88 \times 10^5$ | b) Experiment 2

In this experiment, the base permeation layer was made as above in experiment 1. The attachment layer was grafted using a slurry mixture of 5 mg Meth-SHA and 6 mg AIBN in 300 µl 33% DMSO/67% water. 100 µl of the slurry was loaded onto the array base permeation layer and heated for 1 hour at 80° C. The treated array was then rinsed with DMSO, water, and dried. A control array was also produced without SHA as immediately above. Table V shows the results of this construct. In this experiment, the probe density is about 3 orders of magnitude greater than the control without SHA.

TABLE V

| Array | moles of SHA | [SHA] (M) | moles of AIBN | [AIBN] (M) | mole % SHA | mole % AIBN | probe density |
|---|---|---|---|---|---|---|---|
| test | $6.7 \times 10^{-6}$ | 0.07 | $1.21 \times 10^{-5}$ | 0.12 | 36 | 64 | $2.14 \times 10^{8}$ +/− $1.82 \times 10^{7}$ |
| control | 0 | 0 | $1.21 \times 10^{-5}$ | 0.12 | 0 | 100 | $5.33 \times 10^{5}$ +/− $6.36 \times 10^{4}$ | c) Experiment 3

Figure 2:
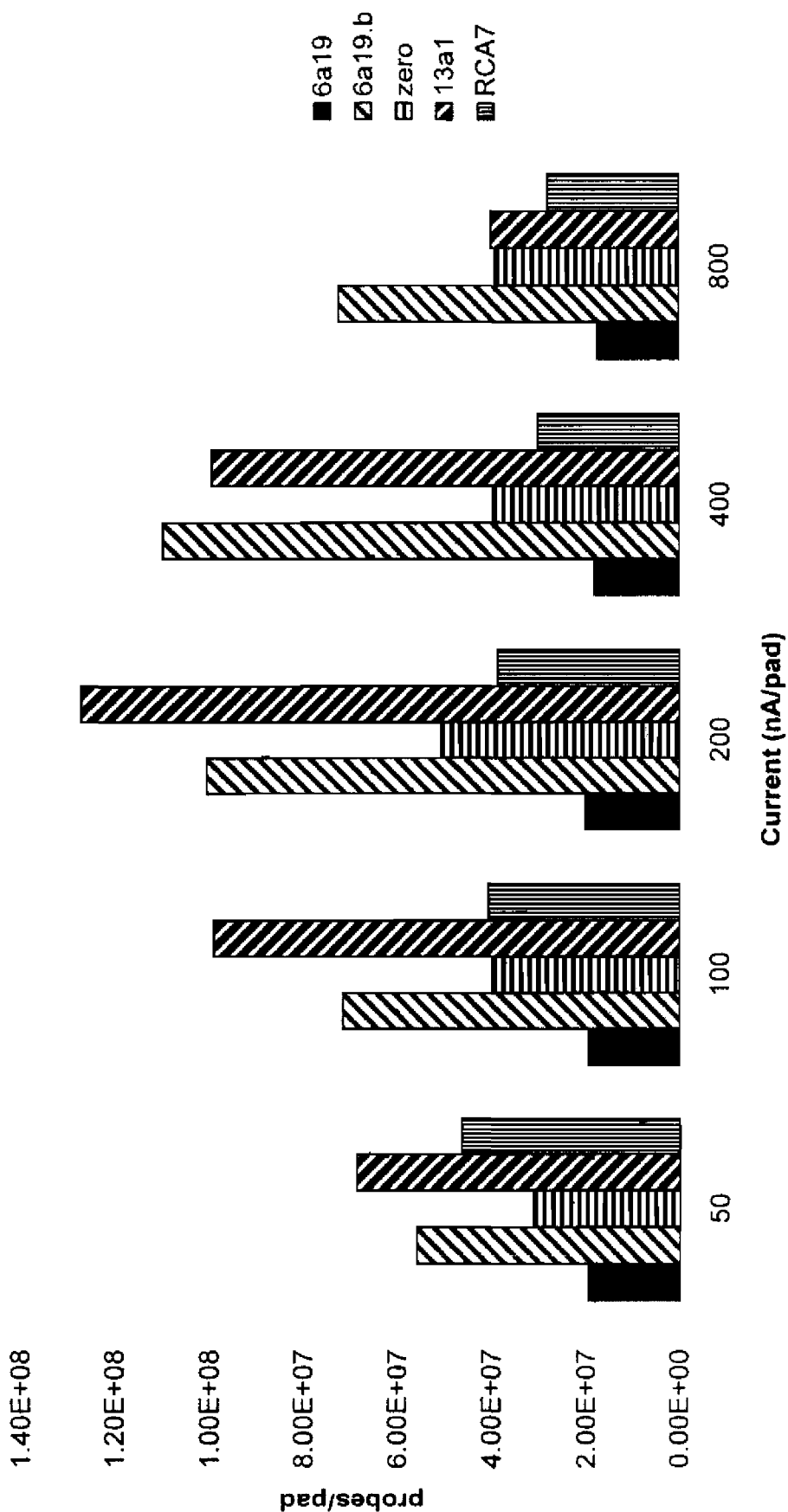
FIG. 2 is a bar graph showing results of an experiment wherein a base permeation layer (30% 9:1 acrylamide/N,N'-methylene bisacrylamide ratio) with bromo-acetopropyl methacrylamide attachment layer was addressed with probe. The probe oligos were present at 500 nM, β-alanine was present at 50 mM. Address time was 30 seconds and the arrays were washed with 0.2×STE and 1% SDS prior to detection.

Microarrays with a base permeation layer were made as above. Attachment layers were constructed on the arrays to test the nature of the binding of the attachment layer to the base layer. A control array was constructed wherein no AIBN was used (i.e. 5 mg Meth-SHA mixed with 300 μl 33% DMSO/67% water of which 100 μl of slurry was layered onto the array and heated for 1 hour at 80° C.). A second control array was produced wherein no SHA or AIBN was used (i.e. 100 μl of 33% DMSO/67% H₂O heated for 1 hour at 80° C.). As shown in the Table VI, the probe density is much lower as compared to the probe density with SHA and AIBN are included as in Table V above. Therefore, AIBN is required for successful grafting of Meth-SHA. Additionally, the results suggest that the Meth-SHA is not merely diffused into the base layer but covalently bound to it. The results also indicate that levels of nonspecific binding obtained in experiments 1 and 2 without AIBN results from true passive nonspecific binding and not due to residual Meth-SHA. This suggestion is derived from the fact that the level of passive nonspecific binding obtained in experiment 3 with no Meth-SHA and no AIBN is actually larger than the signal obtained on the arrays tested in experiments 1 and 2.

with 0.2×STE, 1% SDS, and water then imaged. FIG. 2 shows a bar graph wherein BTR labeled T11 substituted with unreduced disulfide (probe 6a19) gave no binding, BTR labeled T11 unsubstituted (RCA7) gave only background, BTR labeled T11 having a terminal thiol (probe 6a19.b) gave specific attachment, and BTR labeled T11 substituted with phosphorothioate (probe 13a1) gave specific attachment. The specific attachment levels are superior to the levels displayed in example 1 due to the increased number of potential binding sites generated from the graft polymerization technique.

EXAMPLE 3

In this example, chemical moieties for attaching biomolecules at specific locations on the microarray are grafted onto preformed permeation layers. In one embodiment, the grafting method developed for the current invention involves a "solution" method. This method achieves a high density of grafted activation moieties (e.g. substituted acrylamide or methacrylamide monomer) onto acrylamide-based hydrogel permeation layers. In this method, a high concentration of thermally activated initiator is used to obtain grafting onto the preformed permeation layer.

In a preferred embodiment a solution is made of polymerization initiator and attachment monomer which are both

TABLE VI

| Array | moles of SHA | [SHA] (M) | moles of AIBN | [AIBN] (M) | mole % SHA | mole % AIBN | probe density |
|---|---|---|---|---|---|---|---|
| no AIBN | $6.7 \times 10^{-6}$ | 0.07 | 0 | 0 | 100 | 0 | $1.00 \times 10^{6}$ +/− $7.20 \times 10^{5}$ |
| no AIBN or SHA | 0 | 0 | 0 | 0 | 0 | 0 | $9.03 \times 10^{5}$ +/− $1.77 \times 10^{5}$ |

Figure 4:
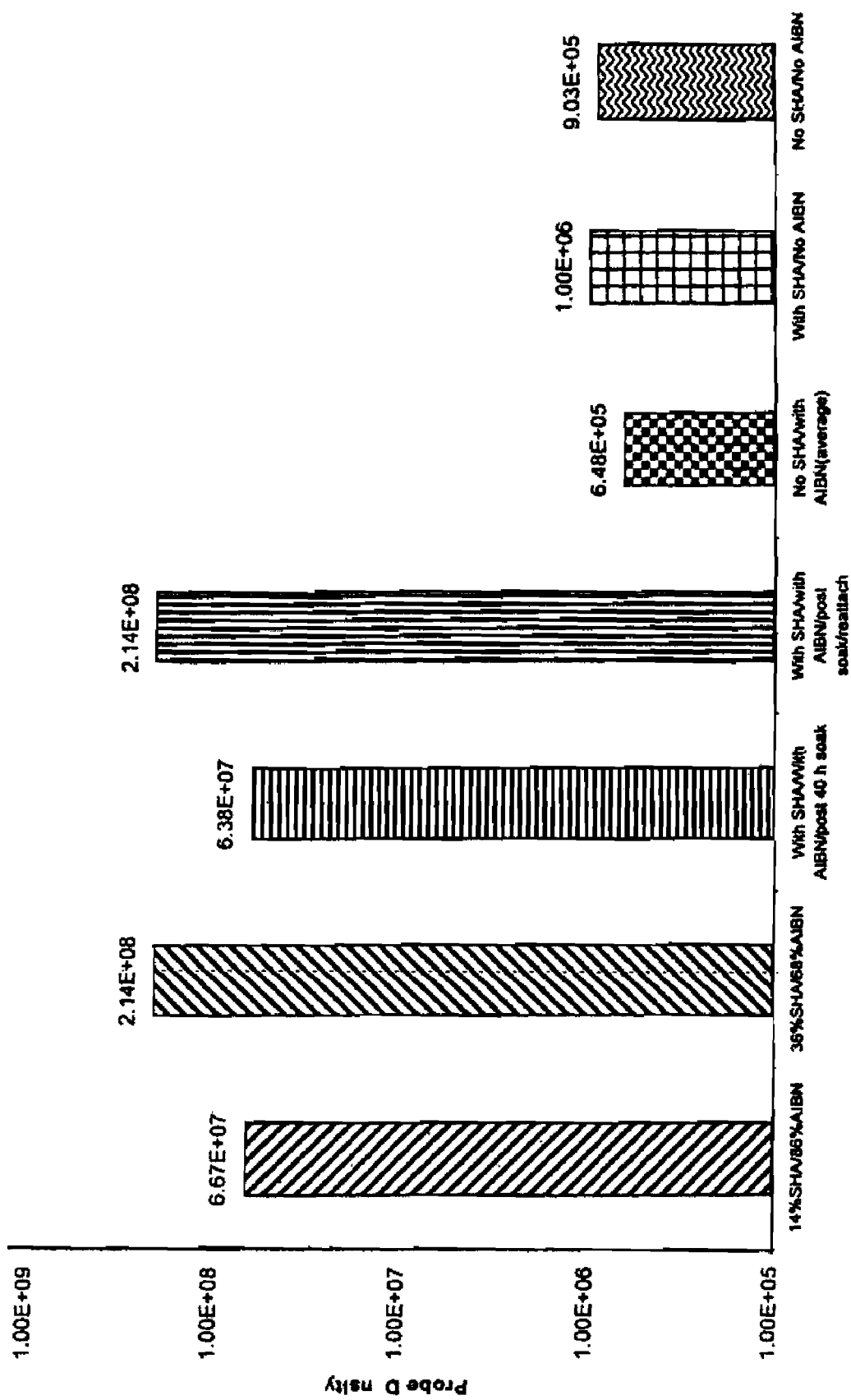
FIG. 4 is a bar graph showing results of grafting experiments using a slurry graft technique. The graph lists densities of probes/pad versus use of various combinations of attachment layer compounds.

FIG. 4 summarizes the results of the above experiments. As shown, attachment levels can result in hybridization of probe densities on the order of $10^{8}$-$10^{9}$ per capture site. Entries 3 and 4 of FIG. 4 show the stability of the attachment chemistry applied. Entry 3 (labeled "With SHA/With AIBN/post 40 hr. soak") shows the mean average binding intensity of entry two after soaking in water for 40 hours, indicating only a slight loss in fluorescence. Entry 4 then shows the recovery of the signal with additional exposure to specific DNA with fluorophor showing the attachment system to the permeation layer has not been compromised.

d) Experiment 4

Microarrays were coated with the standard base permeation layer as described above in experiment 1. They were then slurry grafted with bromoacetyl-propyl-methacrylamide (BacMac) using AIBN as initiator (5 mg BacMac, 5 mg AIBN, 80° C. for 1 hour), then vigorously washed under standard conditions.

Binding assays were carried out using BTR labeled probes that were modified with either terminal thiol, terminal phosphorothioate, unreduced disulfide, or no modification. The probes were electronically addressed to the capture sites in 50 mM β-alanine, 30 seconds, and currents of 50, 100, 200, 400, and 800 nA per site. After addressing, the arrays were washed soluble at room temperature. The solution is applied to the base permeation layer of a microarray then the temperature is then raised to activate the initiator, which results in a high concentration of initiator radicals and monomer locally near the surface of the preformed polymer layer. Attachment of the monomer (i.e., grafting) and polymerization of the monomer occurs simultaneously resulting in covalent attachment of polymerized functional group to the permeation layer. In this manner, the biomolecule attachment moieties (i.e., R moieties) are segregated mainly to the upper region of the polymer layer and consequently are isolated from any deleterious effects that may be caused by electrolysis products of the underlying electrodes or direct electrochemical oxidation at the electrodes.

In comparison to systems which have the attachment sites originating only from the available sites on the substrate layer, the grafted system of the current invention significantly increases the density of sites for attaching biomolecules and consequently allows for a decreased background due to nonspecific binding.

Attachment of the grafted monomer to achieve covalent linkage may be initiated by any number of methods. For example, grafting may use thermal decomposition of initiators (e.g. AIBN, benzoyl peroxide), photolytic cleavage of initiators (e.g. UV initiation of D 4265), redox reactions (e.g. cerium (IV) sulphate), ionizing radiation (e.g. α, β, γ or X-rays), or plasma initiation (e.g. Argon, Nitrogen, Oxygen). Moreover, the grafting process may also be specifically directed to predetermined locations of the array by using chemical moieties that must be activated prior to reaction.

EXAMPLE 3

Experiment 1

In this experiment, the base permeation layer was made as above in experiment 1 of example 2. The attachment layer was grafted using a solution of 5 mg Meth-SHA and 6 mg AIBN in 300 µl DMSO. 100 µl of the solution was loaded onto the array base permeation layer and heated for 1 hour at 80° C. The treated array was then rinsed with DMSO, water, and dried.

Figure 17A:
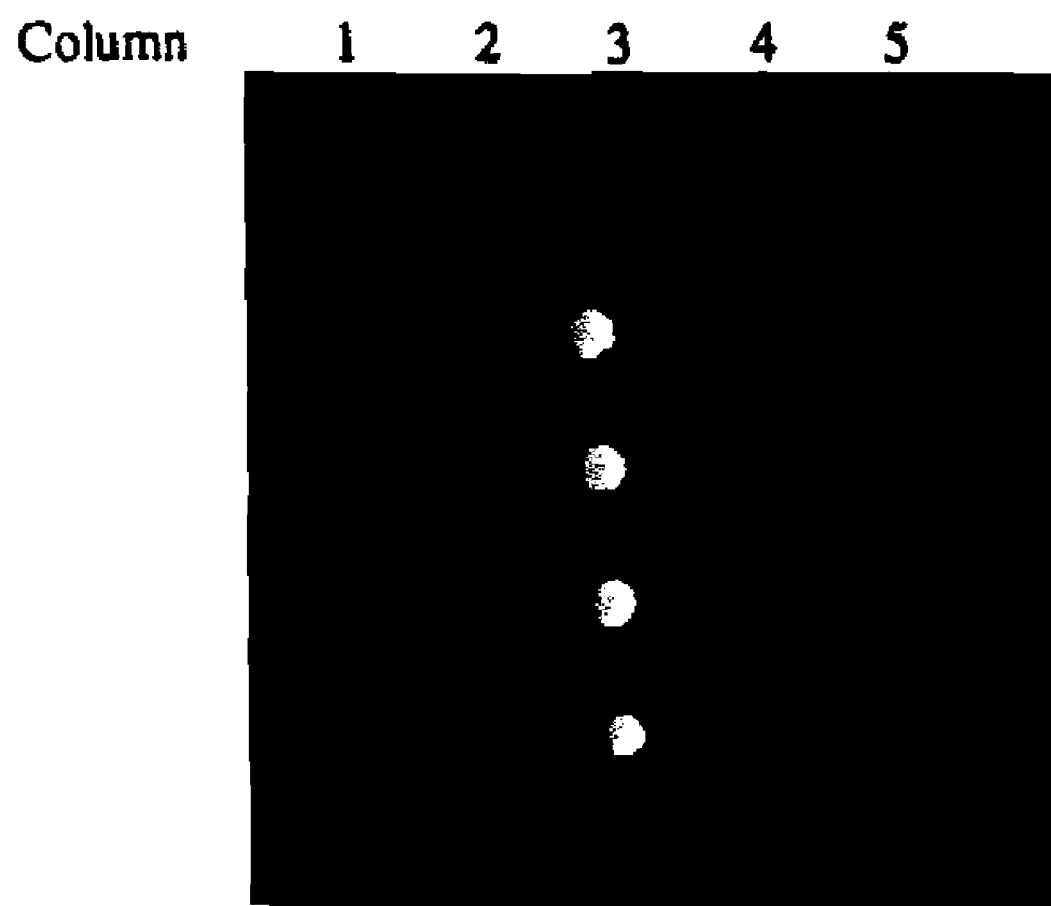
FIGS. 17A and B show results of probe attachment density following solution grafting of a SHA methacrylamide derivative.
Figure 17B:
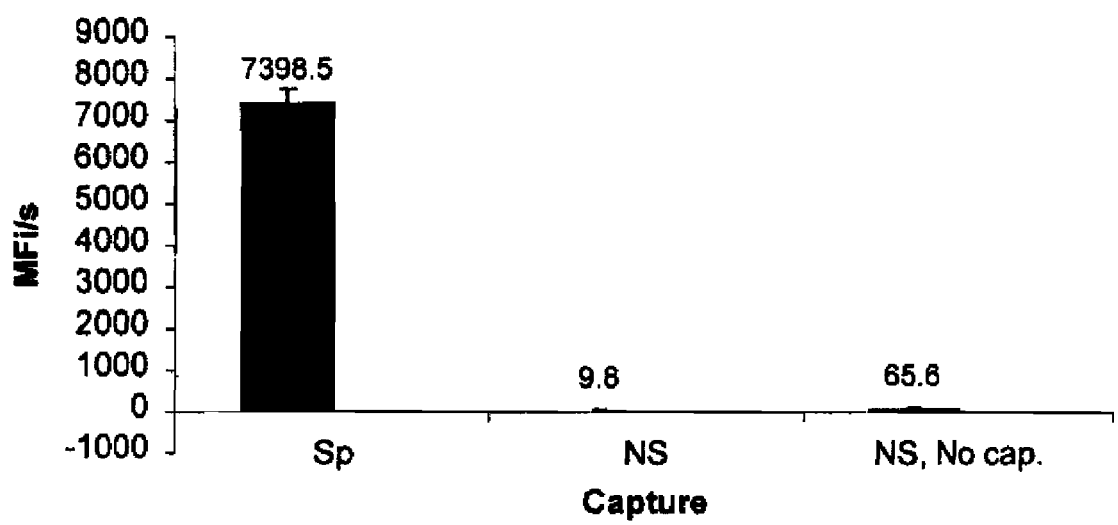
FIG. 17B shows the relative intensities of specific and nonspecific binding.

FIG. 17B is a bar graph showing results of an electronic reverse dot blot assay wherein, the capture probes were addressed at 500 nA/pad for 1 min followed by a specific and nonspecific BTR labeled 69-mer target addressing (500 pM concentration), at 400 nA/pad for 2 min. The chips prior to imaging were washed extensively with 1% SDS and 0.2× STE.

Column 3 was addressed with a specific target, column 1 and 5 were addressed with a nonspecific target and columns 2 and 4 were left unaddressed. The image was recorded after stringent washing as described above as shown in FIG. 17A. The bar graph as shown in FIG. 17B shows a high discrimination for the specific binding of the BTR labeled target with a specific binding of $7 \times 10^7$ probes/pad. The results of the above experiments demonstrate the utility of the solution graft method in laying down a primary layer of individual functional groups for attachment of biomolecules as well as other functional groups.

EXAMPLE 4

Figure 5:
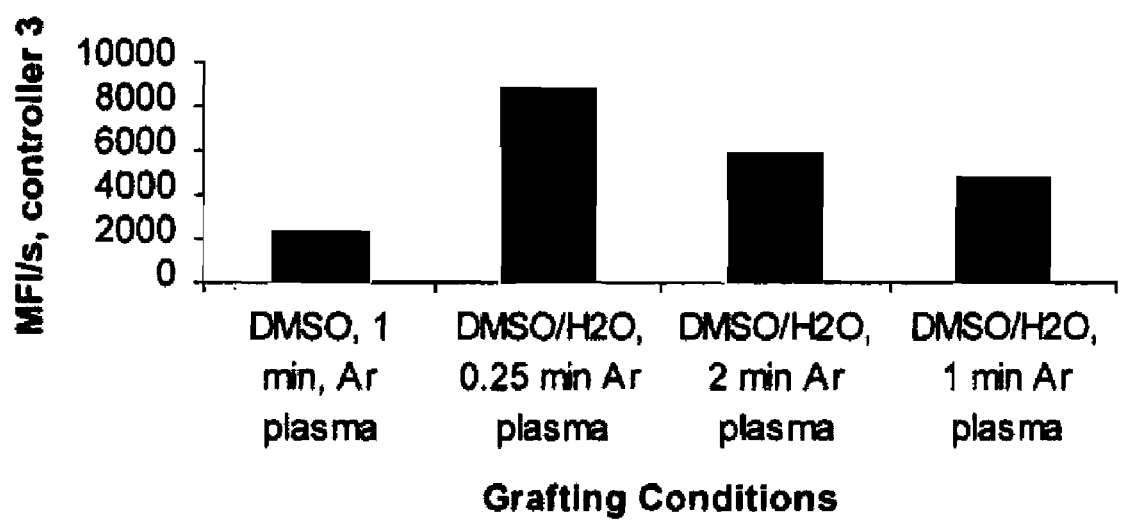
FIG. 5 is a bar graph showing passive attachment of probes following a plasma graft method employing various plasma graft conditions.
Figure 6:
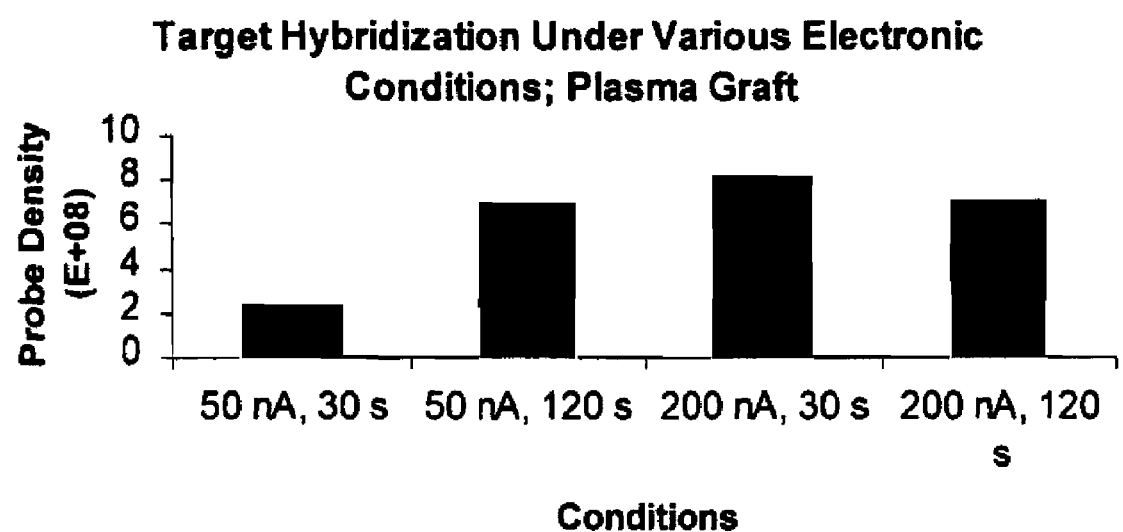
FIG. 6 is a bar graph showing electronic attachment of probes following a plasma graft method. The graph depicts probe binding levels under various addressing conditions.

Additional experiments were performed wherein a "plasma graft" method was used. In this embodiment, arrays were coated with a base permeation layer comprising 9:1 acrylamide/bis-acrylamide wt/wt. The arrays were then treated with argon plasma (50W, 100SCCM) followed by coating with a solution of methacrylamide-salicylhydroxamic acid (MA-SHA) in either DMSO, or 1:1 DMSO/H$_2$O for 5 minutes. The arrays were washed with water and dried. Extent of grafting was determined by either passive or electronic attachment of PBA-T12-BTR probes. FIG. 5 shows passive binding of PBA-T12-BTR probes on arrays that had been grafted under various conditions. Specifically, these arrays gave probe densities of about $2 \times 10^7$ per capture site under conditions where the array was grafted with argon plasma for 1 minute (FIG. 5 shows corresponding MFI/s levels). FIG. 6 shows binding of probe following various electronic addressing conditions on arrays that were grafted with argon plasma for 2 minutes. Attachment levels for arrays that were electronically addressed approached $1 \times 10^7$ probes per capture site (electronic biasing at 200 nA for 30 seconds). By comparison, slurry grafting yielded attachment levels in the range of $2 \times 10^8$ probes per site.

EXAMPLE 5

In this example, a permeation layer is formed that has reactive centers R that must be activated prior to attachment with the functional group. Additionally, the example proves the ability to carry out specific attachment using electronic biasing so that bonding of the functional group occurs only at capture sites of the array.

Figure 7:
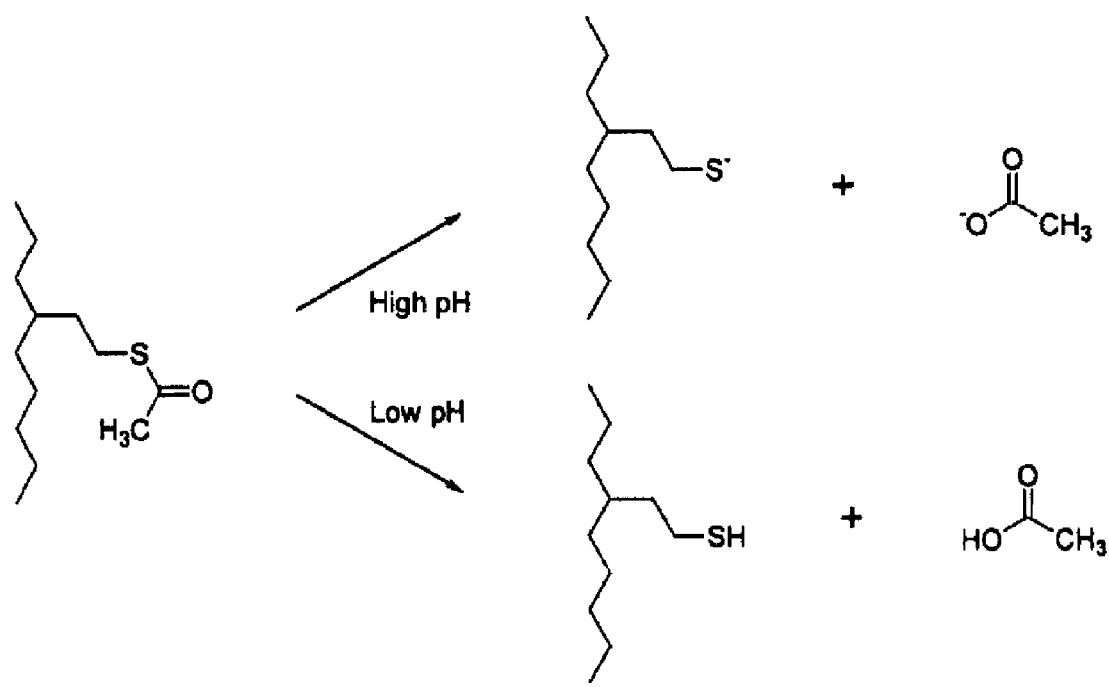
FIG. 7 is a schematic showing that thioester cleavage by either high or low pH will yield an activated thiol group that can in turn be bonded to a chemical moiety for attaching a biomolecule or bonding of a chemical moiety for attaching a polymer.

A base permeation layer was fabricated from an aqueous solution (30% solids) of 3-aminopropyl methacrylamide hydrochloride (APMA) methylene bis-acrylamide (BIS) and acrylamide (Am) using a mole % ratio of 5-5-90 respectively. N,N,N'-Tetramethyl ethylenene diamine (TEMED) was added at a concentration of 0.2% v/v followed by 0.5 g/ml of ammonium persulfate at a final concentration to the monomer mix at 0.2% v/v. 7.5 µl of this solution was placed over the array of a previously silanized (3-trimethoxysilylpropyl methacrylate or TMSPM) electronically addressable microchip and then covered with a glass cover slip that was previously treated with a hydrophobic silicone solution (such as Rain-X™ made by Blue Coral—Slick 50 Ltd.; Cleveland Ohio). The monomer solution was allowed to polymerize at room temperature for 90 minutes. The coated microchip was removed from the cover slip and washed thoroughly to remove residual monomers. The coated microchip bearing free amines was then allowed to react with a solution of 4-(Nhydroxysuccinimidyl)-4-mercapto-(methylester) butanate (SATP) 1.5 mg/ml in DMSO and phosphate buffer pH 7.5, 0.1 M. After reacting overnight, the microchip was washed with buffer, DMSO, and water to remove unbound SATP. The reaction of SATP with amines yields thioesters, hence the derivatization of the permeation layer. The thioester functional groups provided the permeation layer surface with the ability to contain free thiols after further exposure to high or low pH conditions (i.e., activation). FIG. 7 shows a schematic of free thiol generation.

Activation of the thioesters was accomplished by biasing the specific microelectrode locations (i.e. capture sites) with either a positive or negative bias. However, in order to ensure that the pH change remained localized over the electrode, the appropriate buffer system was selected during biasing conditions. If the buffer conditions are too strong, the pH change over the electrode may be minimal or eliminated thereby hindering the activation of the functional groups. Also, if the buffer is too weak, the pH change will not be localized making possible activation of the permeation layer beyond the location of the capture site. In addition, the appropriate current was selected during the biasing procedure. Too little current will not generate the sufficient pH changes needed to hydrolyze the thioester bond. Also if the current is too great, the buffer will have a difficult time keeping the pH change localized.

Figure 8:
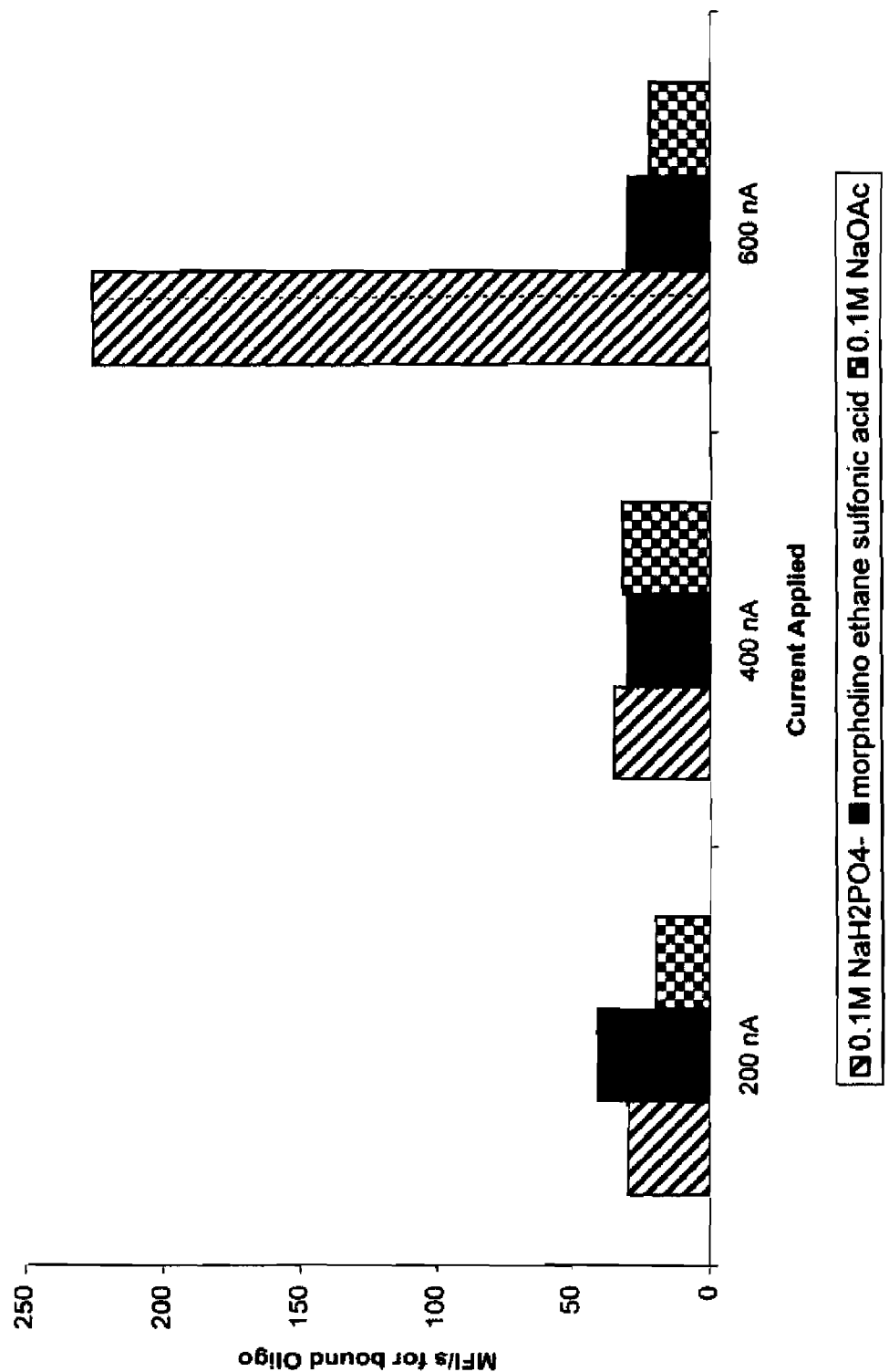
FIG. 8 is a bar graph showing detection or lack thereof of labeled DNA oligomer at the capture sites following electronically generated pH change to assist functional group attachment. The graph depicts results of attachment using three 0.1M $NaPO_4$/triethylamine, pH 6.8; morpholino ethane sulfonic acid; and sodium acetate.

In the example, the three buffer conditions were compared. In one experiment the buffer comprised 0.1 M sodium phosphate pH 6.8, 1 mM triethylamine. The capture sites (80 µm diameter) were biased at a current of 600 nA per location for one minute. A nucleotide of 20 bases that had a 3' Hex fluorophore and a 5' iodoacetamide, a thiol reactive functional group, was prepared as a 20 µM solution in 0.1 M sodium phosphate solution pH 7.5, 1 mM EDTA. The DNA oligomer was then allowed to passively react with the activated microchip permeation layer. After washing the chip with buffer and water several times, the microchip was imaged under an epifluorescence microscope. As shown in FIG. 8, the Hex labeled DNA attached to the capture pads to a very high ratio over background when 600 nA/pad was used to bias the attachment sites. This result shows the need for appropriate buffer systems and the sensitivity to the level of current needed to generate a suitable pH change for generation of thioester cleavage and subsequent functional group attachment. The non-phosphate buffers at the current used in these tests provided no useful effect on local pH at the capture sites.

Figure 9:
FIG. 9 is a schematic showing the specific activation of thioesters at capture sites (microlocations) followed by specific binding of biomolecules only at such capture sites and capping of unreacted groups at noncapture site locations. In this figure, the deposition chemistry has included use of both nonelectronic deposition and specific electronic biasing to achieve attachment of high density biomolecule attachment.
Figure 9:
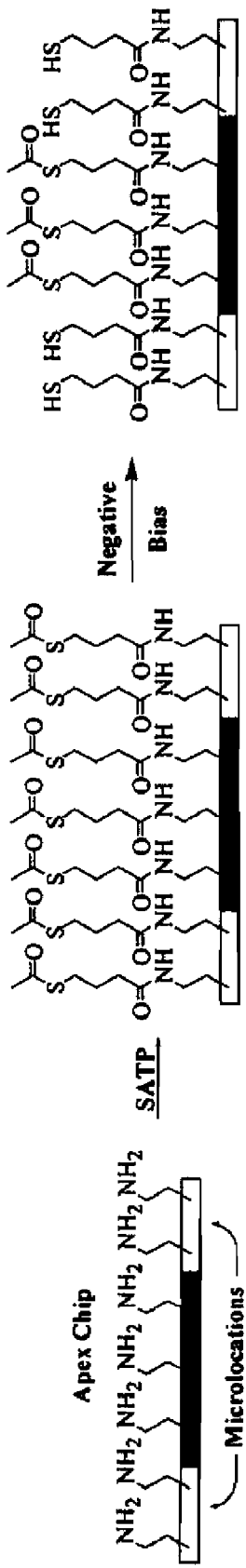
Figure 9:
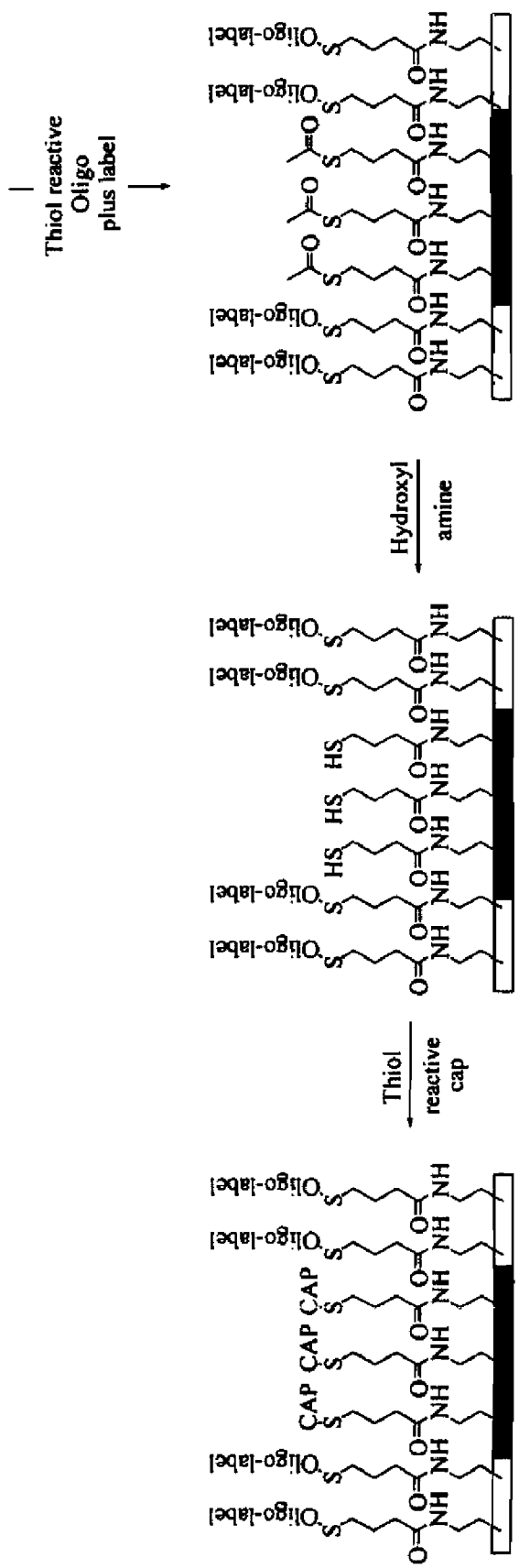

FIG. 9 shows another embodiment of this example wherein a microchip that has had thiol groups attached at specific capture sites and that were reacted with labeled oligomer, were further treated to cause unreacted thiol groups to become inert through the use of a capping moiety, thereby further enhancing the specificity of the microchip capture sites.

The groups requiring activation that may be used according to this example further include a variety of acid labile moieties such as acetals, ketals, imines, TBOC, FMOC, trityl, trifluoroacetamide, other esters, and moieties capable of elimination or hydrolysis. Base labile moieties useful in this embodiment include esters, amides, substituted phosphates, tosyl, mesyl, triflate, and β-cyanoethyl moieties capable of elimination or hydrolysis.

The moiety requiring activation may also be used to specifically attach proteins such as enzymes, via the protein's intrinsic moieties or via modifications that add selected moieties.

EXAMPLE 6

In this example, an embodiment is provided wherein reactive centers R comprise a moiety that must be activated prior to attachment of derivatized biomolecules. The example shows that P and R moieties of functional groups may vary depending upon the desired method of attaching biomolecules.

Acetal moieties are incorporated into the hydrogel formation such that when activated, aldehyde groups are formed specifically over the capture sites to the exclusion of the non-capture site array surface. Use of acetal groups provides a functional group that can be reacted under a variety of conditions thereby allowing for the use of a variety of chemical reagents and transformations to attach biomolecules at capture sites. For example, the reaction of an aldehyde reactive group with dihydrazides allows for attachment of oxidized ribose terminated oligonucleotides. Another example is the direct reaction of the aldehydes with amine terminated oligonucleotides. Likewise, it is also possible to react the aldehydes with amine groups of proteins such as streptavidin for binding to biotinylated oligonucleotides.

In this embodiment, a reactive center R containing an acetal moiety is incorporated into a hydrogel formulation to yield a permeation layer that contains acetal functionality. This acetal functionality may be activated and converted to an aldehyde functionality via electrochemical generated acid hydrolysis of the acetal groups. The electrochemical oxidation of water is used to generate the acidic conditions required to hydrolyze the acetals. The aldehyde groups are then used to link biomolecules such as oligonucleotides to the permeation layer using a P—X—R functional group by a variety of attachment schemes such as use of oxidized ribose oligonucleotides with dihydrazides, amine terminated oligonucleotides, and biotinylated oligonucleotides and streptavidin.

Specifically, acetal monomers such as used in this example (3,9-divinyl-2,4,8,10-tetraoxaspiro[5,5]undecane, and 2-vinyl-1,3-dioxolane) were incorporated into a permeation layer matrix by copolymerization in a crosslinked acrylamide hydrogel. The result is a hydrogel layer coated onto the array which contains acetal functionality. The acetal groups were subsequently hydrolyzed to aldehyde groups via electrochemically generated acid. The low pH required for hydrolysis is generated by electrochemical oxidation of water in 0.1 M KCl solution. The aldehydes were then used as attachment sites for P—X—R functional groups and consequently oligonucleotide biomolecules.

Figure 10:
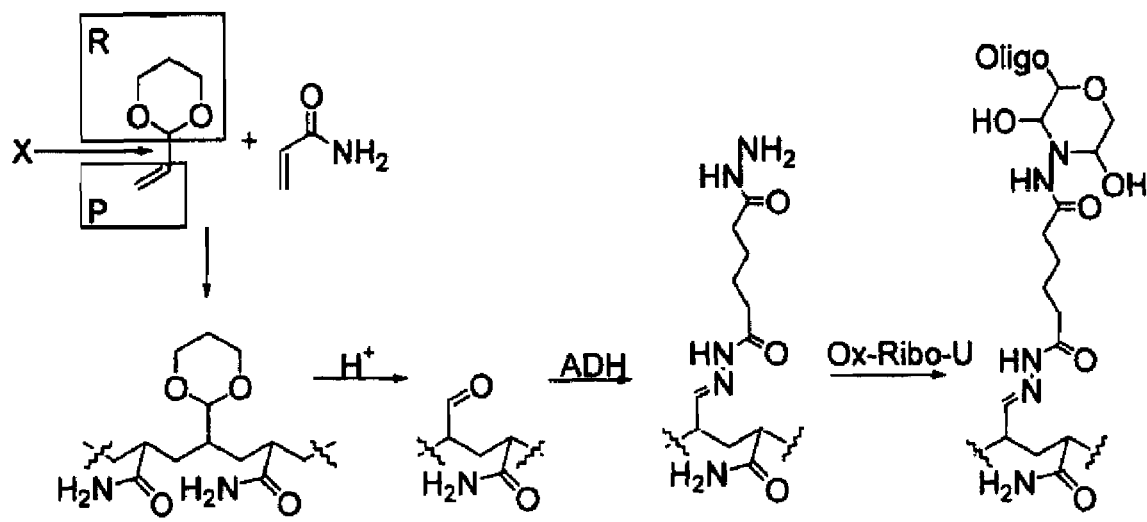
FIG. 10 shows three reactive sequences for different attachment schemes employing acetal reactive centers.
Figure 10:
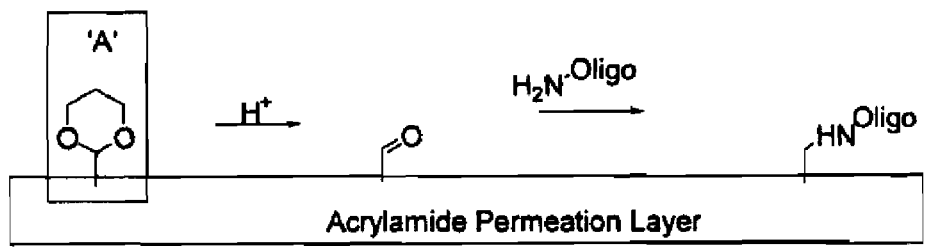
Figure 10:
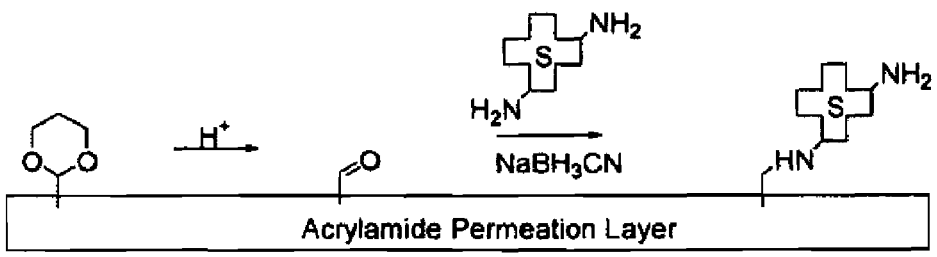

Three attachment schemes were evaluated. In scheme 1, aldehydes were converted to hydrazide via reaction with adipic dihydrazide followed by treatment with oxidized ribose terminated oligonucleotides. The acetals were introduced via copolymerized 2-vinyl-1,3-dioxolane. In scheme 2 the aldehydes were reacted with amine terminated oligonucleotides. In this case the acetals were introduced via copolymerization of 2-vinyl-1,3-dioxolane, In scheme 3, the aldehydes were reacted with amine groups on streptavidin (S) and subsequently attached to biotinylated oligonucleotides. This scheme was used on crosslinked acrylamide hydrogels grafted with either 2-vinyl-1,3-dioxolane or 3,9-divinyl-2,4,8,10-tetraoxaspiro[5,5]undecane. Specific details of these schemes are provided below (refer to FIG. 10). The use of different functional groups in these schemes shows that acetal functionality is universal to different functional groups of the formula P—X—R. Moreover, it demonstrates that the attachment can be controlled to specific sites of interest.

Example 6 Experiments a) Scheme 1

A hydrogel base permeation layer was made comprising 92.5% acrylamide, 5% methylene-bisacrylamide and 2.5% 3,9-divinyl-2,4,8,10-tetraoxaspiro[5,5]undecane. (30% solids) The hydrogel coated microarray was extensively cleaned using an agron plasma (10 minutes) prior to polymerization of the hydrogel layer. Polymerization was initiated by addition of 3 mg/ml of VAO44 as a UV initiator and exposure to UV light. Subsequent heating to 65° C. for 10 minutes was used to ensure complete curing. DMSO/$H_2O$ (50/50 v/v) was used as solvent.

The microarray contained 5 rows of 5 capture sites each. Rows 1, 3 and 5 were biased at 600 nA/site for 2 minutes in 0.1M KCl and thoroughly rinsed with water. The microarray was then immersed in a 1 ml 0.1M phosphate pH 7 solution containing 32 mg/ml of adipic dihydrazide for 1.5 hours. After thorough rinsing with water the array was incubated for 20 minutes with 10 μM oxidized ribo-U ATA5 in 0.1 M phosphate buffer pH 7.4. The array was rinsed with 0.2×STE/1% SDS, then rinsed with 0.2×STE to remove any oxidized ribo-U ATA5. The array was then incubated for 20 minutes with 10 μM RCA5 labeled with Bodipy-Texas Red in 0.1 M phosphate/50 mM NaCl buffer pH 7.4. (ATA5 and RCA5 are perfect complements of one another) Following hybridization the array was rinsed with 0.2×STE/1% SDS, then rinsed with 0.2×STE to remove any RCA5 labeled with Bodipy-Texas Red.

Figure 11:
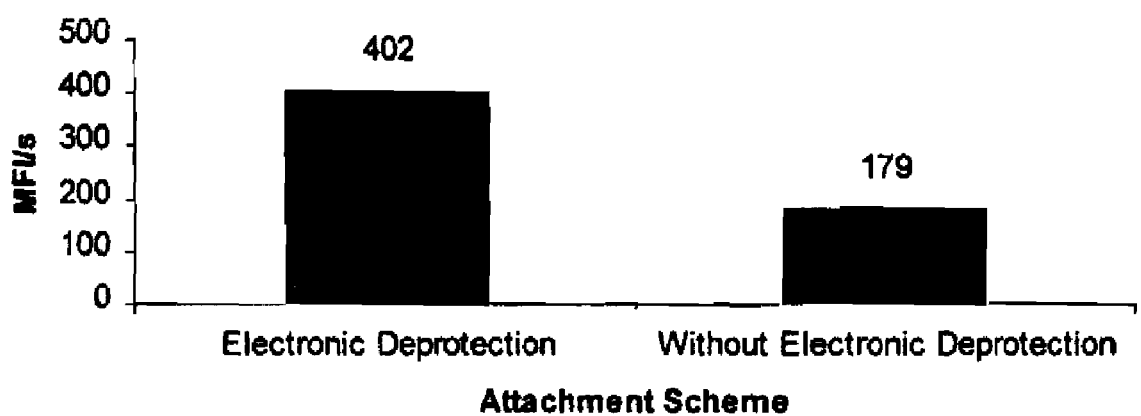
FIG. 11 is a bar graph showing results from an embodiment wherein specific capture sites containing acetal groups were activated (Scheme 1 of FIG. 10).

The 3,9-divinyl-2,4,8,10-tetraoxaspito[5,5]undecane is an acetal-containing compound which forms aldehydes when exposed to low pH. Biasing of the specific sites at 600 nA/site for 2 minutes in 0.1 M KCl generated an appropriate level of protons which hydrolyzed the acetal groups. These aldehyde groups were then reacted with a P—X—R functional group (i.e., adipic dihydrazide) which attached to the aldehydes only at the capture sites which had been biased positive. The oxidized ATA5 oligo (i.e., derivatized biomolecule) has a dialdehyde group which was then reacted with the R moiety hydrazide. FIG. 11 shows attachment results of a labeled biomolecule RCA5-BTR to ATA5 following either specific activation at selected sites or without specific activation (i.e. nonspecific binding). Hybridization has occurred over background where specific activation of positive biasing at 600 nA per site for 2 minutes was used.

b) Scheme 2

In this embodiment, the hydrogel base permeation layer was composed of 85% acrylamide, 5% methylene-bisacrylamide and 5% 2-vinyl-1,3-dioxolane. The microarray was extensively cleaned using an argon plasma (10 minutes) prior to polymerization of the hydrogel layer. Polymerization was initiated by addition of 0.3 mg/ml of D 4265, as UV initiator and exposed to UV light. Subsequent heating to 70° C. for 30 minutes was used to ensure curing. DMSO/$H_2$O (50150 v/v) was used as solvent.

Figure 12:
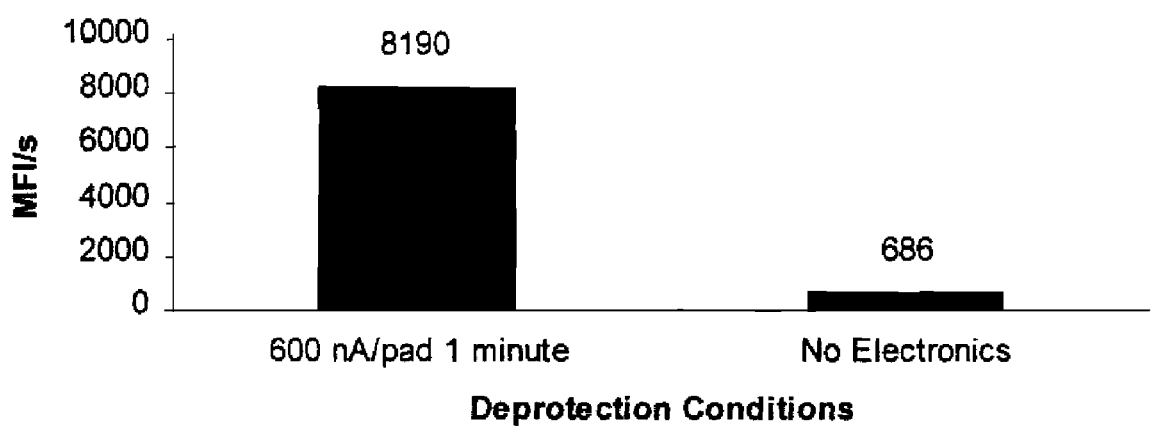
FIG. 12 is a bar graph showing results from an embodiment wherein specific capture sites were activated (Scheme 2 of FIG. 10).

FIG. 12 is a bar graph showing results of specific attachment of a biomolecule wherein the selected capture sites were biased at 600 nA/capture site for 2 minutes in 0.1 M KCl to activate the R moiety acetal to aldehyde. Following activation the array was thoroughly rinsed with water. The microarray was then covered with a 50 µl solution of 0.1M phosphate buffer pH 8 containing 10 µM amine terminated ATA7 labeled with Texas Red. After being incubated for 30 minutes the microarray was rinsed with 0.2×STE/1% SDS, then rinsed with 0.2×STE to remove any unbound amine terminated Texas Red labeled ATA7.

As indicated by FIG. 12, the attachment only occurred at the electrodes which had been biased at 600 nA/capture site for 2 minutes. The attachment levels were about $10^7$ probes per site. This example demonstrated the direct attachment of amine terminated oligonucleotides to the aldehyde groups formed by the electrochemically generated acid hydrolysis of the acetal groups.

c) Scheme 3

In this embodiment, the base permeation layer comprised 90% acrylamide and 10% methylene-bisacrylamide (30% by weight in 1/1 DMSO/$H_2$O). D 4265 was used as UV initiator, and the samples exposed to UV light. The arrays were cured at 60° C. for 1 hour, rinsed, then dried at 60° C.

In this example, the vinyl acetal moieties can be considered to comprise a first P—X—R functional group wherein P is vinyl, X is chemical bond and R is acetal. The acetal moieties were bound to reactive centers of the permeation layer via a "slurry" graft through polymerization of the alkene moiety. This polymerization process exemplifies the applicability of the slurry graft method.

The slurry approach uses a solvent system in which the initiator and functional group are incompletely soluble at room temperature, thus creating a slurry of initiator and functional group. The particles of initiator and functional group settle out onto the surface of the surface of the permeation base layer. Upon increasing the temperature to 90° C., the initiator becomes reactive and the components of the slurry dissolve to generate a high concentration of functional group and initiator radicals locally near the surface of the preformed polymer base layer. This results in the covalent linking of the attachment moiety P of the functional group to the hydrogel. In this example, the acetal monomer was grafted onto the permeation layer using equal weights of the vinyl acetal and AIBN, which serves as an initiator. 5 mg of monomer and AIBN were dissolved in 100 µl DMSO then precipitated into a slurry with addition of 200 µl of water. The grafting was accomplished by addition of 50 µl of the slurry onto the microarray surface and incubated at 90° C. for 1 hour, followed by copious DMSO and water washes.

A second P—X—R functional group was added in the form of streptavidin wherein P is amine X is chemical bond and R is streptavidin This functional group was linked to the activated sites (in this case an R moiety comprising aldehyde) following electronic deprotection (300 nA/capture site at 45-60 seconds in 0.1M KCl). This step caused electrochemical generated acidic hydrolysis of the acetal groups to form aldehydes directly over the capture sites of interest. The streptavidin functional group (1 mg/ml) was applied passively for 1 hour followed in turn by a sodium cyanoborohydride wash (1 hour).

The above steps were carried out on a test microarray wherein columns 1-4 were grafted with the acetal and activated to generate the aldehyde moieties to which functional group streptavidin was added. Column 5 was left as an acetal surface for investigating non-specific attachment. Columns 1 and 3 were electronically addressed with 50 nM biotinylated T12 labeled with Bodipy Texas Red at 400 nA per electrode for 2 minutes. Columns 2 and 4 were electronically addressed with 50 nM non-biotinylated T12 labeled with Bodipy Texas Red. Thus, columns 1 and 3 provided specific attachment while columns 2 and 4 provided for non-specific attachment. The microarrays were then washed in 0.2×STE, 1% SDS for at least 10 minutes, rinsed, and soaked in 0.2×STE for an additional 10 minutes. Finally, the arrays were rinsed in water and imaged in histidine buffer.

Figure 13:
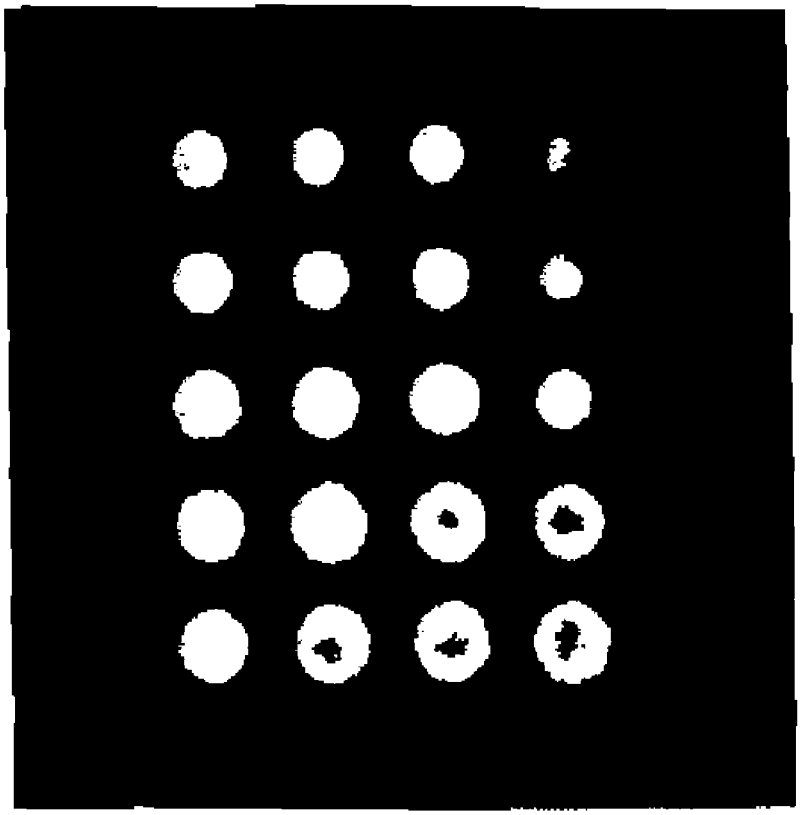
FIGS. 13 to 16 are photomicrographs showing various results of specific activation and binding of labeled probes (Scheme 3 of FIG. 10).

FIG. 13 shows results of the above fabricated microarray wherein the entire array was exposed to biotin T12-BTR as a 10 µM solution for 1 hour. As shown, binding occurred at columns 1-4 but not column 5, i.e., binding occurred only at the sites that had been specifically activated.

Figure 14:
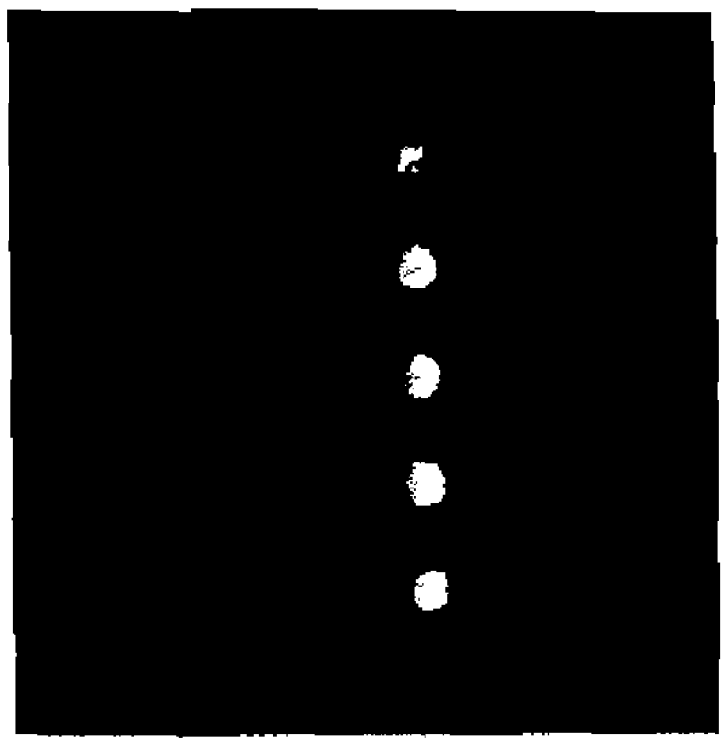

In FIG. 14, an array was produced as above but columns 1 and 2 were activated for 30 seconds at 300 nA/site, while columns 3 and 4 were exposed for 60 seconds. Following activation, the array was reacted with streptavidin and electronically addressed with a specific capture onto columns 1 and 3, while columns 2 and 4 were addressed with nonspecific probes (i.e. nonbiotinylated oligo). Fluorescence analysis of the capture sites provided an indication of the amount of electronic activation is important to bonding of the functional group. As shown, column 1 does not have a fluorescence intensity as compared with column 3 indicating the lack of streptavidin over the sites of column 1. Thus, the time for activation under the conditions used were not enough to provide complete activation at column 1 sites. It is of interest that the fluorescence values recorded for columns 1, 2, and 4 have comparable values as shown in FIG. 14. The fact that the oligo used in column 4 lacked biotin for binding to the streptavidin, while columns 1 and 2 lacked sufficient streptavidin, suggests that nonspecificity may in part be due to the current driving the oligos into the porous permeation layer.

Figure 15:
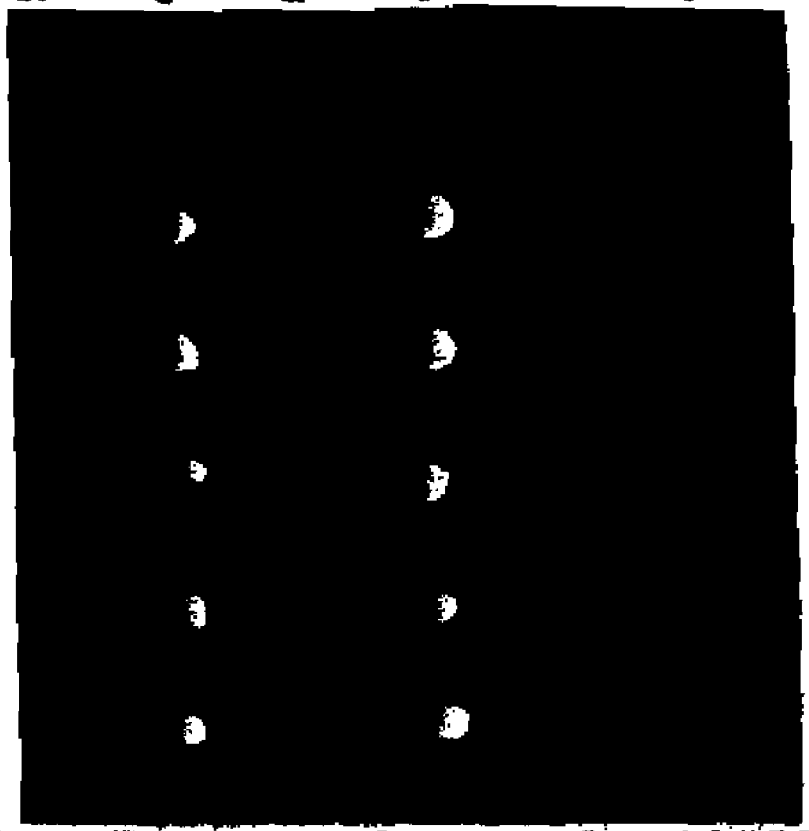
Figure 16:
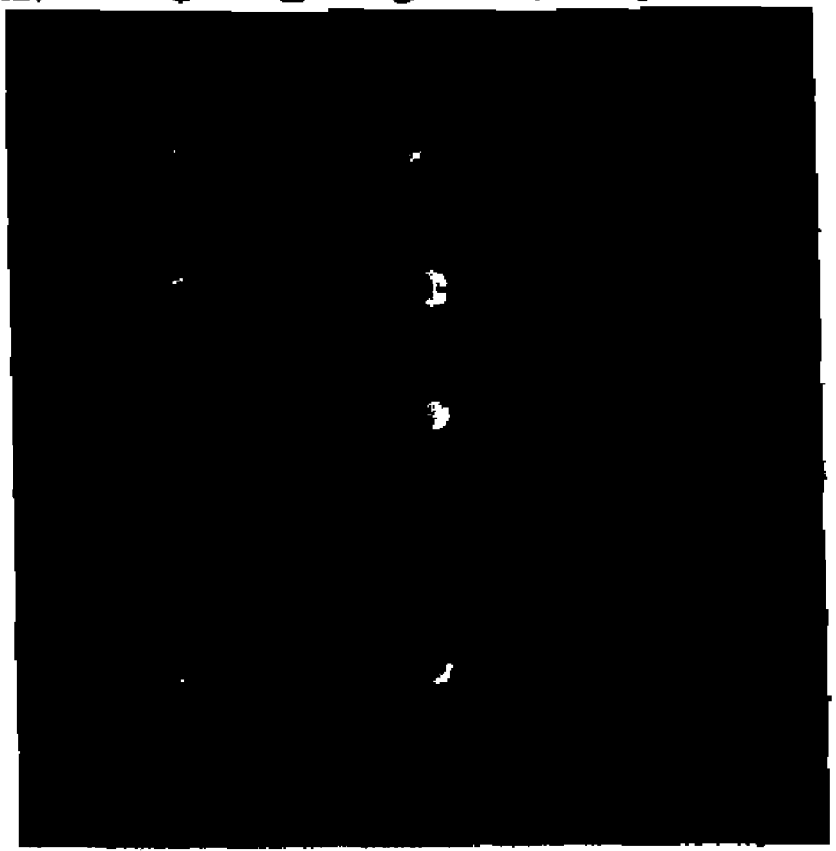

To further test nonspecific binding, an array was prepared as above. Columns 1 and 3 were addressed with biotin T12-BTR followed by washing the array with 50 mM histidine buffer, followed in turn by addressing columns 2 and 4 with nonbiotinylated probe. As shown in FIG. 15, the specific versus nonspecific binding is well pronounced. The fact that some background was observed in columns 2 and 4 prompted yet further investigation shown in FIG. 16 wherein biotin T12-BTR was addressed to columns 1, 3 and 5, followed by washing and imaging. As shown, columns 1 and 3 hybridized as expected while column 5 which had never been activated exhibited marginal background. These data suggest that both passive binding and oligo trapping takes place to result in marginal levels of background.

The results of the above experiments demonstrate the utility of the slurry graft method in laying down a primary layer of individual functional groups (i.e., acetal) and of binding a second functional group layer (i.e., streptavidin moieties). Additionally the results show the utility of activating functional moieties at specifically selected sites on the microarray using electrochemically generated pH changes in the buffer. Further, the grafting of the functional groups to the hydrogel polymer permeation layer and the electronic addressing of oligoncleotides provides information on the levels of specific and nonspecific attachment. Moreover, for either the 2-vinyl-1,3 dioxolane or the 3,9-divinyl-2,4,8,10-tetraoxaspiro[5,5]undecane functional groups, the specific electronic attachment density was on the order of $10^8$ probes per site, while the non-specific was 10 to 100 times less.

The foregoing is intended to be illustrative of the embodiments of the present invention, and are not intended to limit the invention in any way. Although the invention has been described with respect to specific modifications, the details thereof are not to be construed as limitations, for it will be apparent that various equivalents, changes and modifications may be resorted to without departing from the spirit and scope thereof and it is understood that such equivalent embodiments are to be included herein. All publications and patent applications are herein incorporated by reference to the same extent as if each individual publication or patent application was specifically and individually indicated to be incorporated by reference.

What is claimed:

1. A method of addressing a biomolecule to a selectively addressable electrode, comprising the steps of:
   providing a permeation layer overlying a plurality of selectively addressable electrodes, the permeation layer comprising a reactive group adapted to bond to a biomolecule, wherein the reactive group requires activation through a chemical transformation before bonding to the biomolecule;
   biasing at least one selectively addressable electrode such that a pH change occurs in an overlying solution of the at least one selectively addressable electrode, wherein the reactive group in a portion of the permeation layer above the at least one selectively addressable electrode is chemically transformed to an activated reactive group as a result of the pH change; and
   binding a biomolecule to the permeation layer overlying the at least one selectively addressable electrode through the activated reactive group.

2. The method of claim 1, wherein the reactive group is an acid labile group.

3. The method of claim 2, wherein the acid labile group is selected from the group consisting of imines, TBOC, FMOC, trityl, trifluoroacetamide, and esters.

4. The method of claim 2, wherein the reactive group is a thiol ester.

5. The method of claim 2, wherein the reactive group is a ketal.

6. The method of claim 1, wherein the biomolecule is covalently attached to the reactive group.

7. The method of claim 1, wherein the biomolecule is a nucleic acid.

8. The method of claim 1, wherein the biomolecule is selected from the group consisting of proteins, peptides, enzymes, and antibodies.

* * * * *